United States Patent [19]
Joseph et al.

[11] Patent Number: 5,554,269
[45] Date of Patent: Sep. 10, 1996

[54] NO$_x$ SENSOR USING ELECTROCHEMICAL REACTIONS AND DIFFERENTIAL PULSE VOLTAMMETRY (DPV)

[75] Inventors: Jose P. Joseph; Seajin Oh, both of Palo Alto, Calif.

[73] Assignee: Gas Research Institute, Chicago, Ill.

[21] Appl. No.: 420,121

[22] Filed: Apr. 11, 1995

[51] Int. Cl.$^6$ .................................................. G01N 27/407
[52] U.S. Cl. .................... 204/424; 204/425; 204/426; 204/427; 204/429; 205/781
[58] Field of Search .................... 204/153.1, 153.14, 204/400, 434, 421–429; 205/781

[56] References Cited

U.S. PATENT DOCUMENTS

| | | | |
|---|---|---|---|
| 4,500,391 | 2/1985 | Schmidt et al. | 204/1 |
| 4,805,624 | 2/1989 | Yao et al. | 128/635 |
| 4,874,500 | 10/1989 | Madou et al. | 204/412 |
| 4,897,162 | 1/1990 | Lewandowski et al. | 204/1 |
| 4,900,405 | 2/1990 | Otagawa et al. | 204/1 |
| 4,927,517 | 5/1990 | Mizutani et al. | 204/153.14 |
| 4,988,428 | 1/1991 | Iwakiri et al. | 204/406 |
| 5,034,107 | 7/1991 | Wang et al. | 204/153 |
| 5,304,294 | 4/1994 | Wang et al. | 204/426 |
| 5,397,442 | 3/1995 | Wachsman | 204/153.14 |

OTHER PUBLICATIONS

Willard et al, "Instrumental Methods of Analysis", 5th ed., (1974), p. 649–651.

*Primary Examiner*—T. Tung
*Attorney, Agent, or Firm*—Hopkins & Thomas; Scott A. Horstemeyer

[57] ABSTRACT

A sensor system accurately measures nitrogen oxide (NO$_x$) in a gas mixture via the use of at least one electrochemical sensing cell and differential pulse voltammetry (DPV). The sensor system has a sensor with an electrochemical sensing cell for producing an electrical signal (current, voltage, etc.) indicative of an amount of the nitrogen oxide within the gas mixture. The sensing cell has an electrolyte interposed between an anode electrocatalyst and a cathode electrocatalyst. Significantly, a DPV mechanism is connected to the sensing cell for enhancing the sensitivity and selectivity of the electrolyte associated with the sensing cell. The DPV mechanism has (1) a pulse superimposition mechanism for combining a pulse with a sensing cell bias imposed upon the sensing cell; (2) a measurement mechanism for measuring the electrical signal before and during superimposition of the pulse to derive first and second sample signals; and (3) a concentration derivation mechanism for mathematically combining (preferably, subtraction) the first and second sample signals to derive a DPV signal which is indicative of the NO$_x$ concentration. Optionally, based upon the material structure of the sensing cell, the sensor system may also be equipped with an electrochemical pumping cell for consuming oxygen (O$_2$) within the gas mixture.

16 Claims, 13 Drawing Sheets

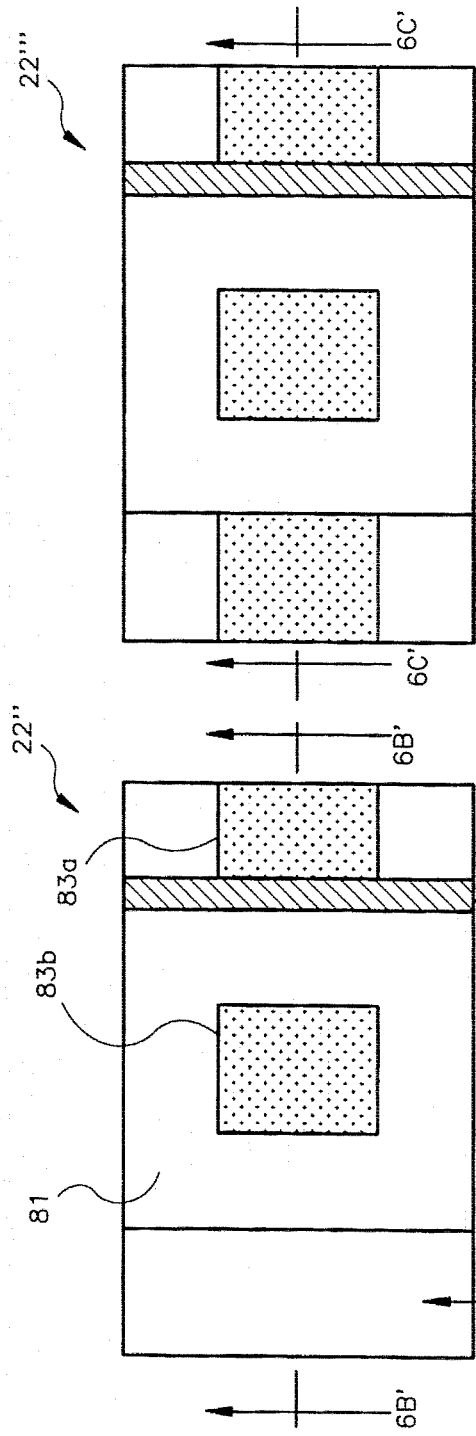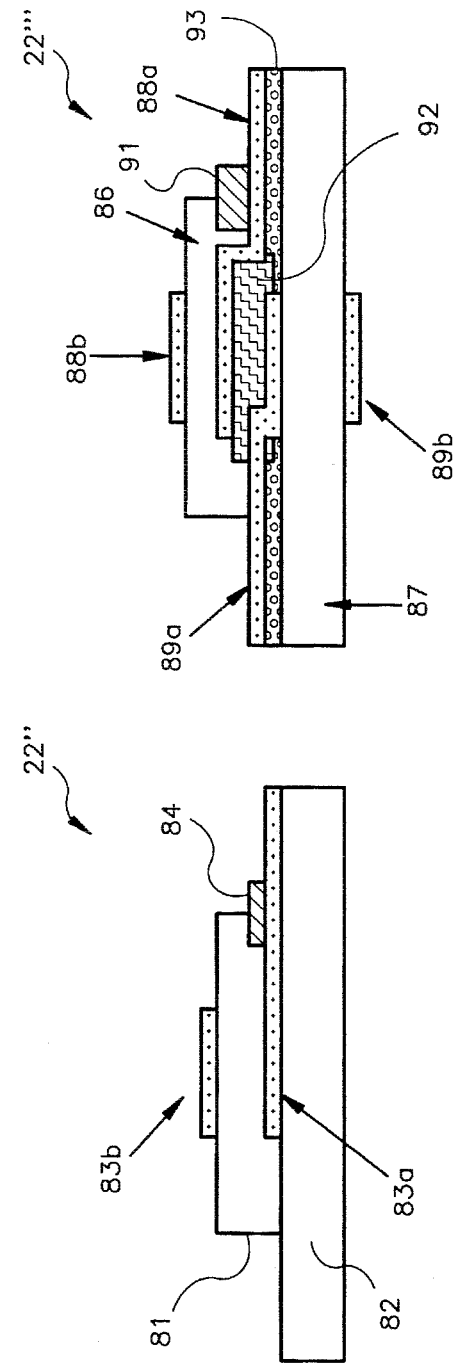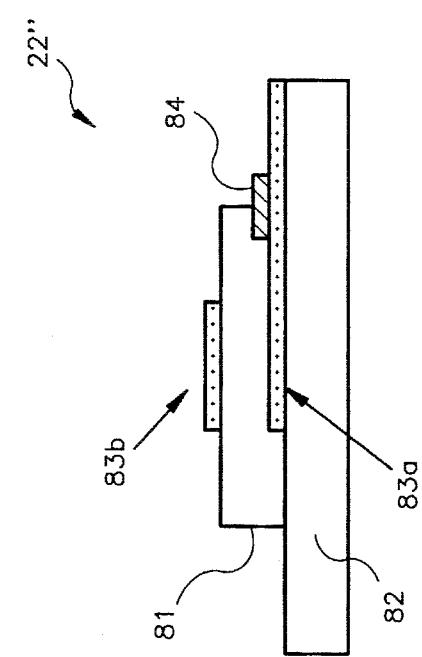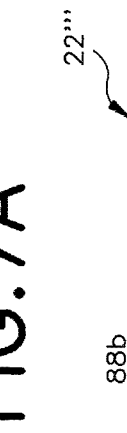

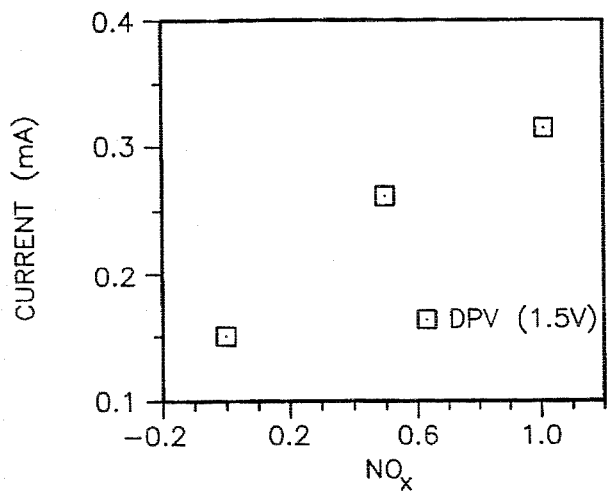
FIG. 15A  $NO_x$ CONCENTRATION 0% – 1%
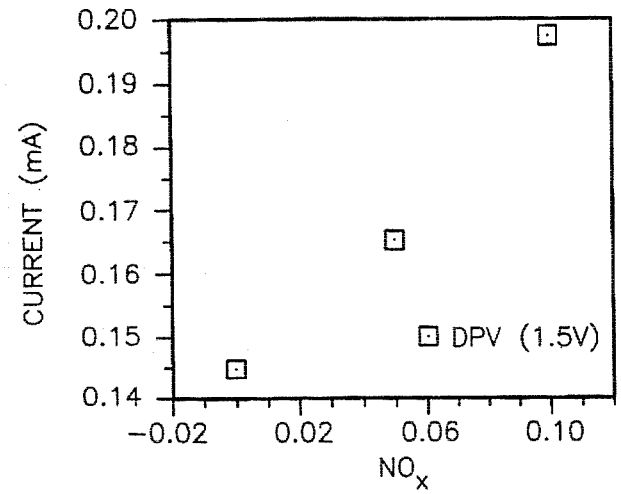
FIG. 15B  $NO_x$ CONCENTRATION 0% – 0.1%
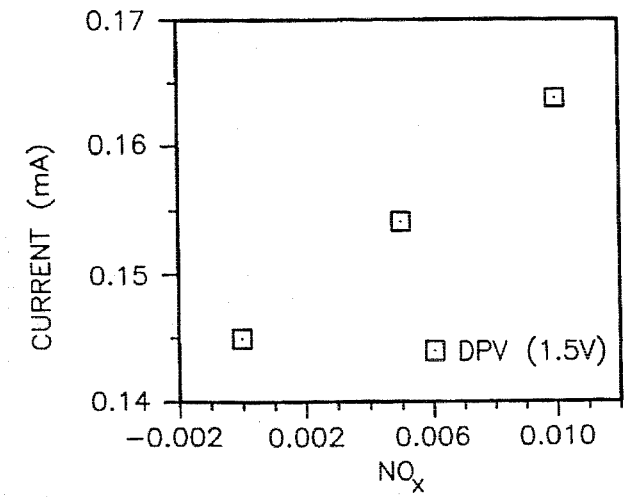
FIG. 15C  $NO_x$ CONCENTRATION 0% – 0.01%

$NO_x$ SENSOR USING ELECTROCHEMICAL REACTIONS AND DIFFERENTIAL PULSE VOLTAMMETRY (DPV)

FIELD OF THE INVENTION

The present invention generally relates to electrochemical analysis and measurement of specific gases within an environment containing a mixture of gases, and more particularly, to a sensor and method for accurately measuring nitrogen oxide ($NO_x$) concentrations in gas mixtures, such as exhaust gases and emissions from combustion engines, furnaces, and facilities, which may contain oxygen ($O_2$), via electrochemical reactions and differential pulse voltammetry (DPV).

BACKGROUND OF THE INVENTION

Nitrogen oxide ($NO_x$, for example, $N_2O$, $NO_x$, $NO_2$, etc.) generated from combustion processes is a serious atmospheric pollutant. In fact, continuous on-line monitoring of $NO_x$ from combustion processes is often necessary to meet strict regulations of the U.S. Clean Air Act, which are expected to become more and more stringent in the future. Furthermore, because the amount of $NO_x$ in the exhaust of a combustion process is indicative of the air/fuel ratio, $NO_x$ concentration can also be used for feedback control of the air-to-fuel ratio of the combustion process in order to achieve optimal fuel efficiency.

Various apparatus and techniques are known in the art for determining the concentration of $NO_x$ in a gas mixture, which may include, for instance, gaseous oxygen ($O_2$), nitrogen ($N_2$), and/or other gases. Typically, the electrochemical sensing of gaseous oxide compounds has been based on a well known "oxygen pumping principle," which is described briefly hereafter. The oxygen pumping principle has been widely publicized and is described in, for example, U.S. Pat. No. 4,005,001 to Pebler, U.S. Pat. No. 4,770,760 to Noda et al., U.S. Pat. No. 4,927,517 to Mizutani et al., U.S. Pat. No. 4,950,380 to Kurosawa et al., U.S. Pat. No. 5,034,107 to Wang et al. and U.S. Pat. No. 5,034,112 to Murase et al.

Generally, a solid electrolyte conductive to oxygen ions is utilized when employing the oxygen pumping principle. The electrolyte is commonly zirconia ($ZrO_2$), bismuth oxide ($Bi_2O_3$), $ZrO_2$ and/or $Bi_2O_3$ containing alkaline earth dopants, such as calcia (CaO), or containing rare earth dopants, such as yttria ($Y_2O_3$), as a stabilizer, or some other suitable electrolyte having the properties more fully described hereafter. These electrolytes show a high permeability (conductance) to oxygen ions $O^{2-}$ when biased at a constant voltage and when maintained above a certain temperature, for instance, greater than 200° C. in many applications. In other words, in an environment containing oxygen, these electrolytes can selectively permit oxygen to pass therethrough if certain biasing and temperature conditions are met. Said another way, these electrolytes exhibit high conductivity at elevated temperatures, and application of a voltage creates an $O^{2-}$ current or flux.

In sensors utilizing these oxygen-ion-permeable electrolytes, electrocatalysts are usually disposed on opposing sides of the electrolyte, and a voltage is applied across the electrolyte via the electrocatalysts. The electrocatalysts typically comprise platinum (Pt), rhodium (Rh) and/or other noble metals. In this configuration, the combination of the electrocatalysts and the electrolyte disposed therebetween forms an electrochemical cell which is often referred to as a "pumping cell" because it pumps oxygen from the gas mixture exposed to the pumping cell. The pumping cell causes oxygen in the gas mixture to be reduced to oxygen ions $O^{2-}$ at the negative electrocatalyst (cathode), and then the oxygen ions $O^{2-}$ move through the electrolyte to the positive electrocatalyst (anode), where they are oxidized to oxygen again and discharged.

Numerous techniques have been proposed in the art for determining the amount of oxygen and/or oxide compounds in the environment around electrochemical cells, particularly pumping cells, by monitoring the voltage and/or current generated across and/or through the electrolyte. A brief discussion of several exemplary types of prior art sensors is set forth hereafter, but it should be noted that this discussion is not exhaustive.

One type of sensor is described in U.S. Pat. No. 5,217,588 to Wang. This sensor employs two electrochemical cells on a zirconian electrolyte. One cell senses only oxygen gas and the other cell senses all the gases which contain oxygen, including the oxygen gas. Both electrochemical cells are exposed to the same gas mixture, and the difference between the sensed signals is a measure of the concentration of $NO_x$ in the gas mixture.

Another type of sensor is described in U.S. Pat. No. 5,034,112 to Murase et al. In this sensor, an electrocatalyst for reducing $NO_x$ is placed on an electrolyte adjacent to a pumping cell. A current is induced in the pumping cell so as to control the oxygen concentration in the environment around the pumping cell. When the oxygen concentration is depleted to a predetermined level, the electrocatalyst supposedly begins to deplete $NO_x$, and the concentration of $NO_x$ is determined by measuring the current supplied to the pumping cell.

Although the sensors of the prior art have some merit, they do not provide for highly accurate measurement of $NO_x$ or other oxide compounds in gas mixtures because the electrocatalysts utilized for the electrochemical cells do not provide for sufficient selectivity between oxygen and $NO_x$. In other words, some amounts of oxygen and some amounts of these oxide compounds are undesirably consumed by the wrong electrocatalyst, and this phenomenon results in inaccurate measurements of oxygen as well as $NO_x$ concentrations. Moreover, if the gas mixture contains a relatively low $NO_x$ concentration as compared with that of oxygen, the signal-to-noise ratio is small, and an accurate determination of the $NO_x$ concentration is even more difficult. In exhaust gases or emissions produced by internal combustion engines or furnaces, the concentration of oxygen is typically several thousand times higher than the $NO_x$ concentration. Hence, measurements of $NO_x$ in exhaust gases using the prior art techniques are undesirably and unavoidably inaccurate.

SUMMARY OF THE INVENTION

An object of the present invention is to overcome the inadequacies and deficiencies of the prior art as noted above and as generally known in the industry.

An object of the present invention is to provide a sensor and method for accurately measuring $NO_x$ in exhaust from gas combustion processes.

Another object of the present invention is to provide a sensor with sufficient sensitivity and selectivity so that $NO_x$ can be accurately measured in exhaust from gas combustion processes.

Another object of the present invention is to provide a sensor with sufficient sensitivity and selectivity so that $NO_x$ can be accurately measured in the presence of $O_2$.

Another object of the present invention is to provide an $NO_x$ sensor which is simple in design, reliable in operation, and exhibiting optimal sensitivity and selectivity to $NO_x$ so that $NO_x$ can be accurately measured in exhaust from gas combustion processes and particularly in exhaust having gaseous oxygen.

Another object of the present invention is to provide a method for enhancing the sensitivity and selectivity of an electrolyte, such as one having zirconia ($ZrO_2$), with respect to $NO_x$.

Another object of the present invention is to provide a highly effective $NO_x$ sensor which is inexpensive to manufacture.

Briefly described, the present invention provides for a sensor system and method for accurately measuring $NO_x$ in a gas mixture via the use of differential pulse voltammetry (DPV). The sensor system has an $NO_x$ sensor. The $NO_x$ sensor has an electrochemical sensing cell for producing an electrical signal (current, voltage, etc.) indicative of an amount of the nitrogen oxide within the gas mixture. The sensing cell has an electrolyte interposed between a pair of electrocatalysts, or electrodes, one referred to as the anode and the other the cathode. The electrolyte is formed from yttria-stabilized-zirconia (YSZ), some other ZrOx compound, bismuth oxide ($Bi_2O_3$), $Bi_2O_3$ containing alkaline earth dopants, such as calcia (CaO), or containing rare earth dopants, such as yttria ($Y_2O_3$), as a stabilizer, some other suitable material, or combinations thereof. The electrocatalysts can be made from noble metals, (for example but not limited to, gold (Au), platinum (Pt), or rhodium (Rh)), metal oxides (for example but not limited to, a perovskite), other suitable materials, or combinations thereof.

Optionally, depending upon the material structure of the sensing cell, the $NO_x$ sensor may be further equipped with an electrochemical pumping cell for consuming oxygen ($O_2$) within the gas mixture. The $O_2$ pumping cell is constructed similar to the sensing cell, with a suitable electrolyte interposed between opposing electrocatalysts.

In accordance with a significant feature of the present invention, the sensor system further comprises a DPV mechanism, which is connected to the sensing cell for enhancing the sensitivity and selectivity of the electrolyte associated with the sensing cell. The DPV mechanism has (1) a pulse superimposition mechanism for combining a pulse $v_{pulse}$ with a sensing cell bias $V_{bs}$ imposed upon the $NO_x$ sensing cell; (2) a measurement mechanism for measuring the electrical signal (preferably, current $i_s$) before and during superimposition of the pulse $v_{pulse}$ to derive first and second sample signals; and (3) a concentration derivation mechanism for mathematically combining (preferably, subtraction) the first and second sample signals to derive a DPV signal which is indicative of the $NO_x$ concentration. In the DPV signal, the background noise current due to coexisting gases, such as $NO_x$ and $O_2$, and the capacitive charging is substantially reduced or completely eliminated to provide inherent selectivity and better resolution (i.e., signal-to-background ratio). Moreover, the mathematical operation of combining the first and second sample signals eliminates the effect of drift on the $NO_x$ measurement.

The sensitivity, selectivity, and resolution can be even further enhanced when using DPV if the reduction reactions of coexisting gases, such as $NO_x$ and $O_2$, occur at different electrical potentials. This desirable operation can be accomplished by the use of electrocatalysts which are highly selective to $NO_x$ and $O_2$, respectively.

The physical structure of the $NO_x$ sensor can exhibit many possible configurations. As an example, the sensor could be designed with a single-hole housing having an internal cavity where the pumping cell's cathode and the sensing cell's cathode are disposed. In this configuration, the cavity has only a single hole for ingress and egress of the gas mixture. As another example, the sensor could have a porous layer enclosing one or both of the cathode electrocatalysts corresponding with the cells. In this configuration, the porous layer is permeable to the gas mixture for permitting passage of the gas mixture therethrough to the shielded cathode electrocatalyst.

The electrical biasing of the sensing cell could take many possible forms. However, in the preferred embodiment, the electrical biasing is a periodic voltage signal in the form of a step function waveform. The DPV pulses are superimposed over the step function waveform commencing at a rising edge of the step function waveform and terminating during the step level after the rising edge.

In addition to achieving all of the aforementioned objects, the present invention has many other advantages, a few of which are delineated hereafter.

An advantage of the present invention is that a DPV $NO_x$ sensor system can be used to measure a very small amount of $NO_x$ in the presence of a very large amount of $O_2$ (even as high as about 5% by volume).

Another advantage of the present invention is that DPV can be utilized to make measurements based upon electrocatalysts that are originally nonselective to $NO_x$, ultimately highly selective to $NO_x$.

Another advantage of the present invention is that a DPV $NO_x$ sensor system using either YSZ or some other $ZrO_2$ compound as a sensing electrolyte can be inexpensively manufactured and easily afforded by individual gas consumers.

Another advantage of the present invention is that a DPV $NO_x$ sensor system can provide a linear output over a wide range of $NO_x$ concentrations (100 percent (%) down to a few parts per million (ppm)).

Another advantage of the present invention is that an $NO_x$ sensor in the DPV $NO_x$ sensor system can exhibit long-term operational stability by utilizing very stable electrocatalysts, which would be undesirably nonselective to $NO_x$ without the use of DPV.

Another advantage of the present invention is that YSZ can be utilized in the $NO_x$ sensor of the DPV $NO_x$ sensor system, and YSZ is an extremely stable material in combustion exhaust. In fact, YSZ has been widely used for monitoring automotive exhaust gas and has a lifetime of between 5 to 10 years.

Another advantage of the present invention is that the DPV $NO_x$ sensor system can accurately provide information for feedback control of the air-to-fuel ratio for a combustion process in order to achieve high fuel efficiency.

Another advantage of the present invention is that the DPV $NO_x$ sensor system can be used as an exhaust diagnostic tool for $NO_x$ abating devices.

Another advantage of the present invention is that DPV can be utilized to further enhance the sensitivity and selectivity of metal oxide perovskites relative to $NO_x$ and/or $O_2$. Perovskites utilized as electrocatalysts in electrochemical cells are described in copending application entitled "Sensor And Method For Accurately Measuring Concentrations Of Oxide Compounds In Gas Mixtures", Ser. No. 08/208,449, filed Mar. 9, 1994, by inventor Eric Wachsman, which is now U.S. Pat. No. 5,397,442. The foregoing disclosure is incorporated herein by reference. In the aforementioned document, it was determined that the perovskites $La_2CuO_4$, $LaNiO_3$, $LaFeO_3$, $LaCoO_3$, and $LaSrCoO_3$ were highly selective to $O_2$, and that the perovskites $LaRuO_3$ and $LaMnO_3$ were highly selective to $NO_x$. These selectivities can be further optimized using DPV.

Other objects, features, and advantages of the present invention will become apparent to one with skill in the art upon examination of the drawings and the following detailed description. All such additional objects, features and advantages are intended to be included herein within this disclosure.

BRIEF DESCRIPTION OF THE DRAWINGS

The present invention can be better understood with reference to the following drawings. The drawings are not necessarily to scale, emphasis instead being placed upon clearly illustrating principles of the present invention. Further note that like reference numerals designate corresponding parts throughout the several views.

FIG. 5 shows exploded and cross-sectional views of the single-hole-type $NO_x$ sensor (first embodiment); specifically.

FIG. 6 shows top and cross-sectional views of a single-cell porous-type $NO_x$ sensor (second embodiment); specifically, FIG. 6A shows a top view and FIG. 6B shows a cross sectional view taken along line 6B'—6B';

FIG. 7 shows top and cross-sectional views of another double-cell porous-type $NO_x$ sensor (third embodiment); specifically, FIG. 7A shows a top view and FIG. 7B shows a cross sectional view taken along line 7B'—7B';

FIGS. 15A–15C show graphs of current versus $NO_x$ concentration of DPV measurements using the double-cell porous-type DPV $NO_x$ sensor of FIG. 7 in gas mixtures with varying degrees of $NO_x$ and about 0.5% $O_2$ which is reduced by an $O_2$ pumping cell.

DETAILED DESCRIPTION OF THE PREFERRED EMBODIMENTS

Figure 1:
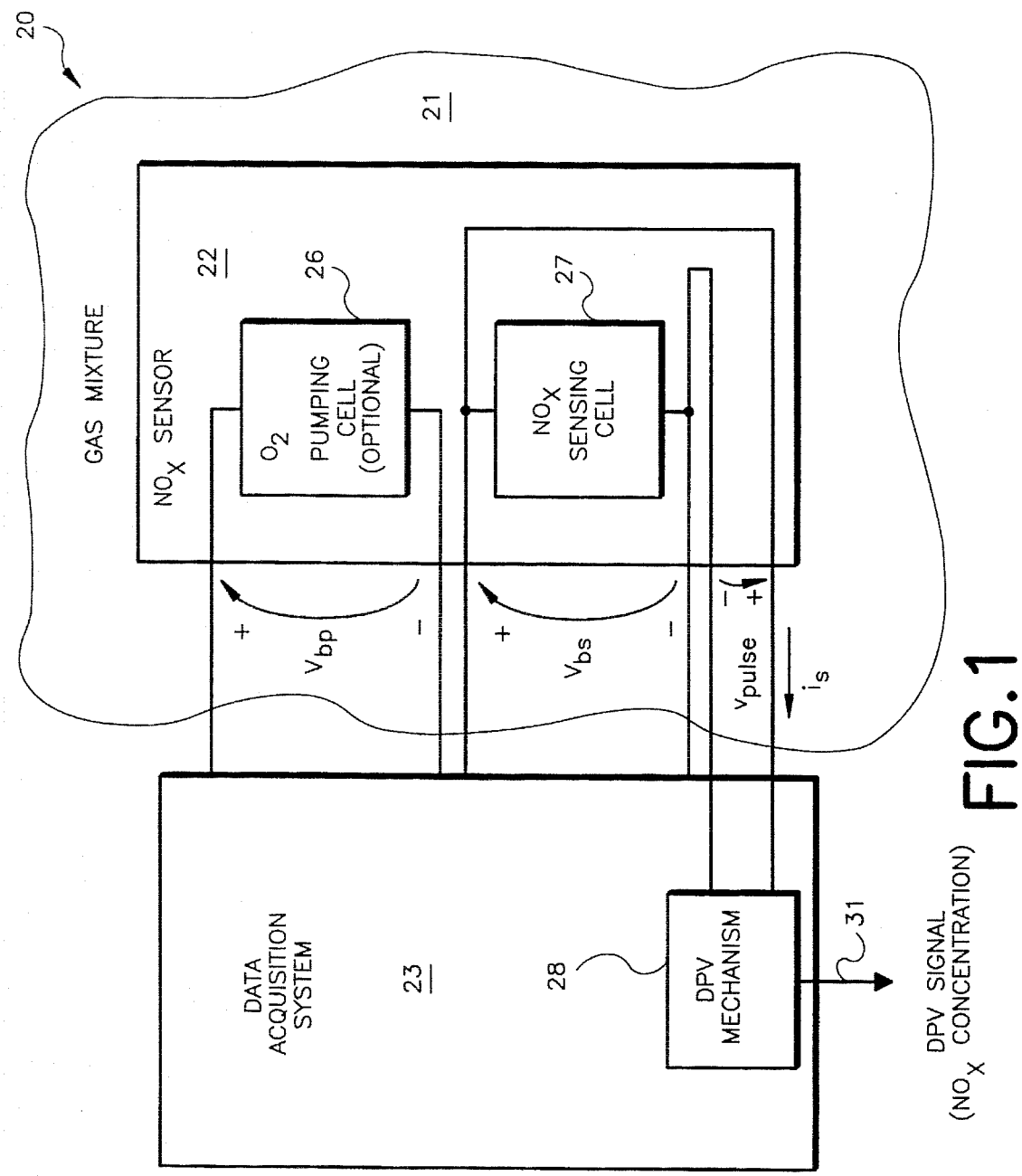
FIG. 1 shows a schematic block diagram of a DPV $NO_x$ sensor system in accordance with the present invention.

FIG. 1 illustrates the DPV $NO_x$ sensor system 20 in accordance with the present invention. The DPV $NO_x$ sensor system 20 can be used for accurately measuring $NO_x$ within a gas mixture 21 via the use of differential pulse voltammetry (DPV). The gas mixture 21 comprises $NO_x$ and possibly other gases, including oxygen ($O_2$). Generally, the DPV $NO_x$ sensor system 20 has an $NO_x$ sensor 22 disposed within the gas mixture 21 and a data acquisition system 23 connected to the $NO_x$ sensor 22 for driving and monitoring the $NO_x$ sensor 22.

The $NO_x$ sensor 22 has an $NO_x$ sensing cell 27 for consuming $NO_x$ within the gas mixture 21. Optionally, depending upon the material and selectivity of the sensing cell 27, as will further become apparent later in this document, an $O_2$ pumping cell 26 may be disposed within the $NO_x$ sensor 22 for consuming $O_2$ within the gas mixture 21. The electrochemical cells 26, 27 each have an electrolyte interposed between an anode electrocatalyst and a cathode electrocatalyst. The electrolyte is formed from yttria-stabilized-zirconia (YSZ), another $ZrO_2$ compound, bismuth oxide ($Bi_2O_3$), $Bi_2O_3$ containing alkaline earth dopants, such as calcia (CaO), or containing rare earth dopants, such as yttria ($Y_2O_3$), as a stabilizer, or another suitable material. The electrocatalysts of the cells 26, 27 are made from gold (Au), platinum (Pt), rhodium (Rh), another nobel metal, or some other suitable material. In order to consume $O_2$, the $O_2$ pumping cell 26 is provided with a voltage bias $V_{bp}$. In order to consume and sense $NO_x$, the $NO_x$ sensing cell 27 is provided with a voltage bias $V_{bs}$.

The data acquisition system 23 provides the voltage biases $V_{bp}$, $V_{bs}$ to the cells 26, 27, respectively. These biases can be DC (steady state) or can vary over time, as is well known in the art. Further, circuits for generating these biases are well known in the art. In accordance with a significant feature of the present invention, the data acquisition system 23 comprises a DPV mechanism 28 for enhancing the sensitivity and selectivity of the $NO_x$ sensing cell 27, particularly the electrolyte corresponding thereto, and produces a DPV signal 31 which very accurately corresponds to the $NO_x$ concentration within the gas mixture 21.

Figure 2:
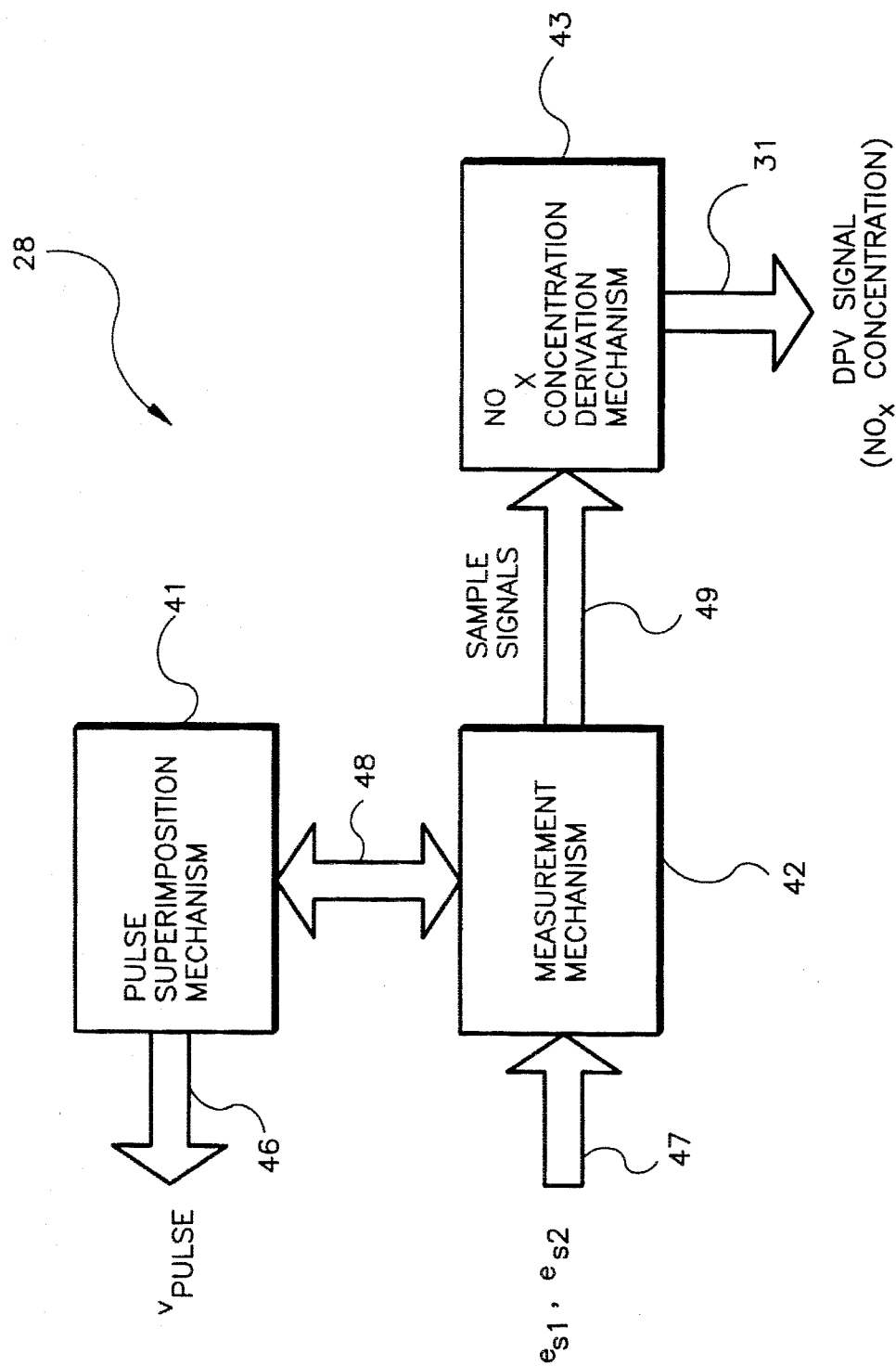
FIG. 2 shows a block diagram of the architecture of the DPV mechanism of FIG. 1.

The DPV mechanism 28 may be implemented in hardware (via, e.g., logic gates), software (via executable instructions), or a combination thereof. As shown in FIG. 2, the DPV mechanism 28 comprises a pulse superimposition mechanism 41 for generating a voltage pulse $v_{pulse}$ and for combining the voltage pulse $v_{pulse}$ with the sensing cell bias $v_{bp}$. A measurement mechanism 42 measures an electrical characteristic e (e.g., current i, voltage v, etc.) of the $NO_x$ sensing cell 27 both before and during superimposition of the voltage pulse $v_{pulse}$ to derive first and second sample signals. Moreover, an $NO_x$ concentration derivation mechanism 43 mathematically combines (e.g., subtraction, as in the preferred embodiment), the first and second sample signals in order to derive the DPV signal 31, which is indicative of the $NO_x$ concentration within the gas mixture 21.

When the DPV signal 31 is derived in accordance with the aforementioned procedure, the noise caused by background current due to coexisting gases, such as $O_2$, and capacitive charging is substantially reduced or completely eliminated. Hence, the inherent selectivity of the sensing cell 27 is enhanced and better resolution (i.e., signal-to-background ratio) is provided. Furthermore, the mathematical operation of combining the first and second sample signals eliminates the effect of drift on the $NO_x$ measurement.

The selectivity and resolution can be even further enhanced when using DPV if the reduction reactions of coexisting gases, such as $NO_x$ and $O_2$, occur at different electrical potentials. This desirable operation can be accomplished by the use of electrocatalysts which are highly selective to $NO_x$ and $O_2$, respectively. For instance, in copending application entitled "Sensor And Method For Accurately Measuring Concentrations Of Oxide Compounds In Gas Mixtures", Ser. No. 08/208,449, filed Mar. 9, 1994, by inventor Eric Wachsman, which is now U.S. Pat. No. 5,397,442, metal oxide perovskites having high selectivity to $NO_x$ and $O_2$ were described. In the aforementioned document, it was determined that the perovskites $La_2CuO_4$, $LaNiO_3$, $LaFeO_3$, $LaCoO_3$, and $LaSrCoO_3$ were highly selective to $O_2$, and that the perovskites $LaRuO_3$ and $LaMnO_3$ were highly selective to $NO_x$.

Figure 3:
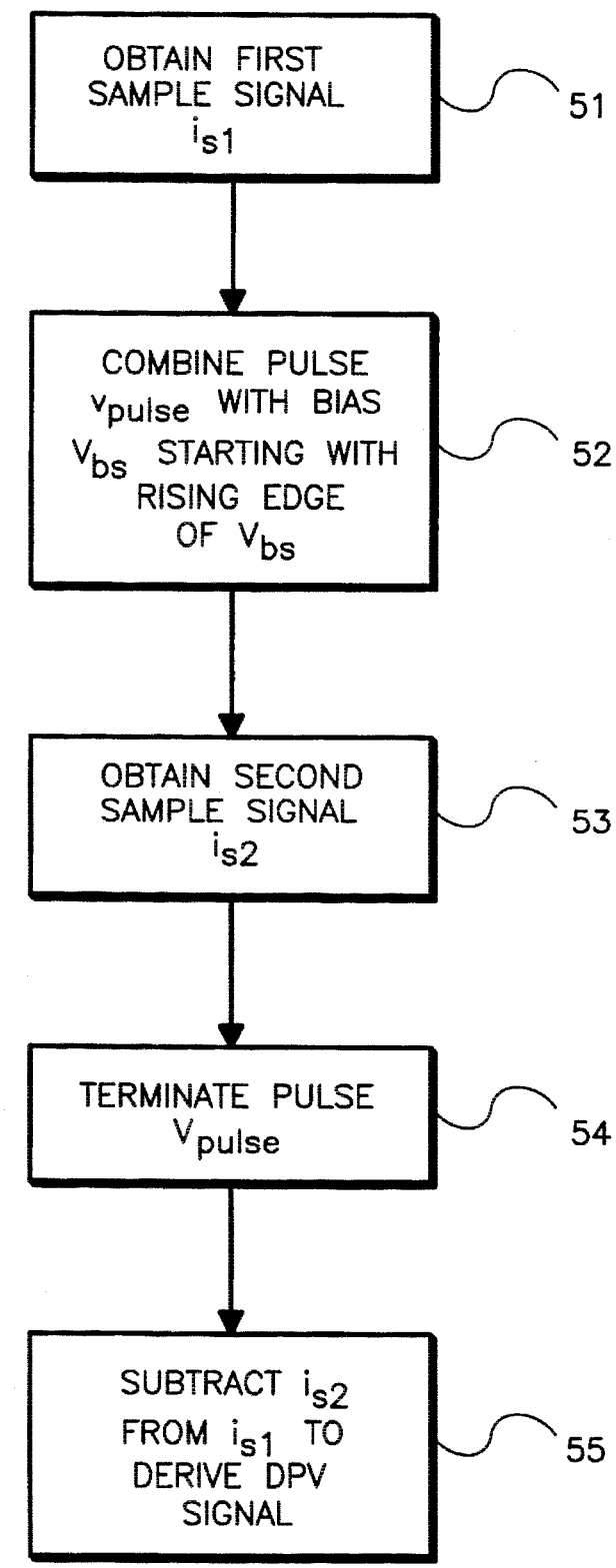
FIG. 3 shows a flow chart indicating the functionality and architecture of a preferred embodiment of the DPV mechanism of FIGS. 1 and 2.

FIG. 3 shows a flow chart indicating the preferred functionality and architecture of the DPV mechanism 28 in FIGS. 1 and 2. In the preferred embodiment, the voltage bias $V_{bs}$ on the $NO_x$ sensing cell 27 is a step function waveform, as is well known in the art. With reference to FIG. 3, particularly block 51, the measurement mechanism 42 (FIG. 2) of the DPV mechanism 28 obtains a first sample signal from the $NO_x$ sensing cell 27 (FIG. 1). In the preferred embodiment, the sample signals are currents $i_s$ (FIG. 1), and the first sample signal is denoted by $i_{s1}$ herein. Next, as indicated in block 52, the pulse superimposition mechanism 41 (FIG. 1) generates a substantially square voltage pulse $v_{pulse}$ and combines the voltage pulse $v_{pulse}$ with the sensing cell bias $V_{bs}$ starting with the rising edge of $V_{bs}$ and terminating during the steady state voltage step just after the rising edge. During the pulse, as indicated at block 53 in FIG. 3, the second sample signal $i_{s2}$ is sensed by the measurement mechanism 42 (FIG. 1) from the $NO_x$ sensing cell 27 (FIG. 1). Moreover, the pulse $v_{pulse}$ is terminated so that the sensing cell bias $V_{bs}$ drops to its steady-state step level, as indicated in block 54 of FIG. 3. Finally, as shown in block 55, the currents $i_{s2}$, $i_{s1}$ are mathematically combined via subtraction in the preferred embodiment by the $NO_x$ concentration derivation mechanism 43 (FIG. 2) in order to derive the DPV signal 31, which is accurately indicative of the $NO_x$ concentration in the gas mixture 21.

Figure 4:
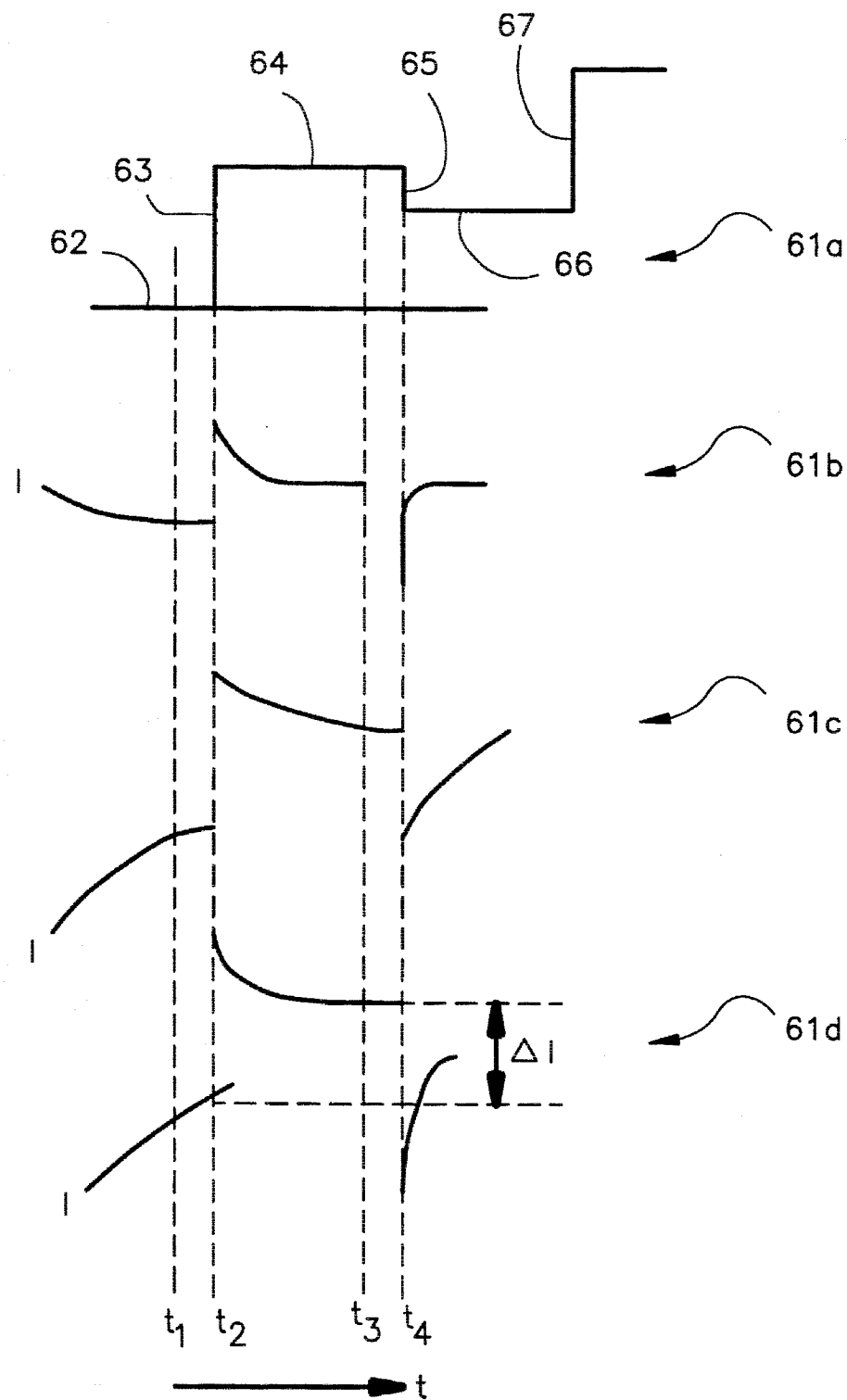
FIG. 4 shows a graph of voltage and current waveforms corresponding with DPV of the present invention.

Reference numeral 61a in FIG. 4 graphically illustrates the resultant bias $V_{bs}$ imposed upon the $NO_x$ sensing cell 27 due to the superimposition of the voltage pulse $v_{pulse}$. As shown in FIG. 4, the step function waveform is initially at the steady state voltage level 62 and the first sample signal $i_{s1}$ is obtained at time $t_1$. The step function then begins to rise at time $t_2$, as indicated by the rising edge 63. During the rising edge 63, the voltage pulse $V_{pulse}$ is generated and additively superimposed on the step function waveform. Reference numeral 64 indicates the steady-state voltage level during the time when the pulse is superimposed on the step function waveform. At time $t_3$, the second sample signal $i_{s2}$ is obtained. Next, the pulse is terminated at time $t_4$ and the voltage level of the step function waveform declines, as indicated by falling edge 65 to another steady-state voltage level 66, which represents the voltage level at which the step function waveform would have assumed after the rising edge 63 if the voltage pulse $V_{pulse}$ had not been superimposed. After the voltage level 66, the step function waveform again begins to rise as indicated by the rising edge 67.

Figure 5A:
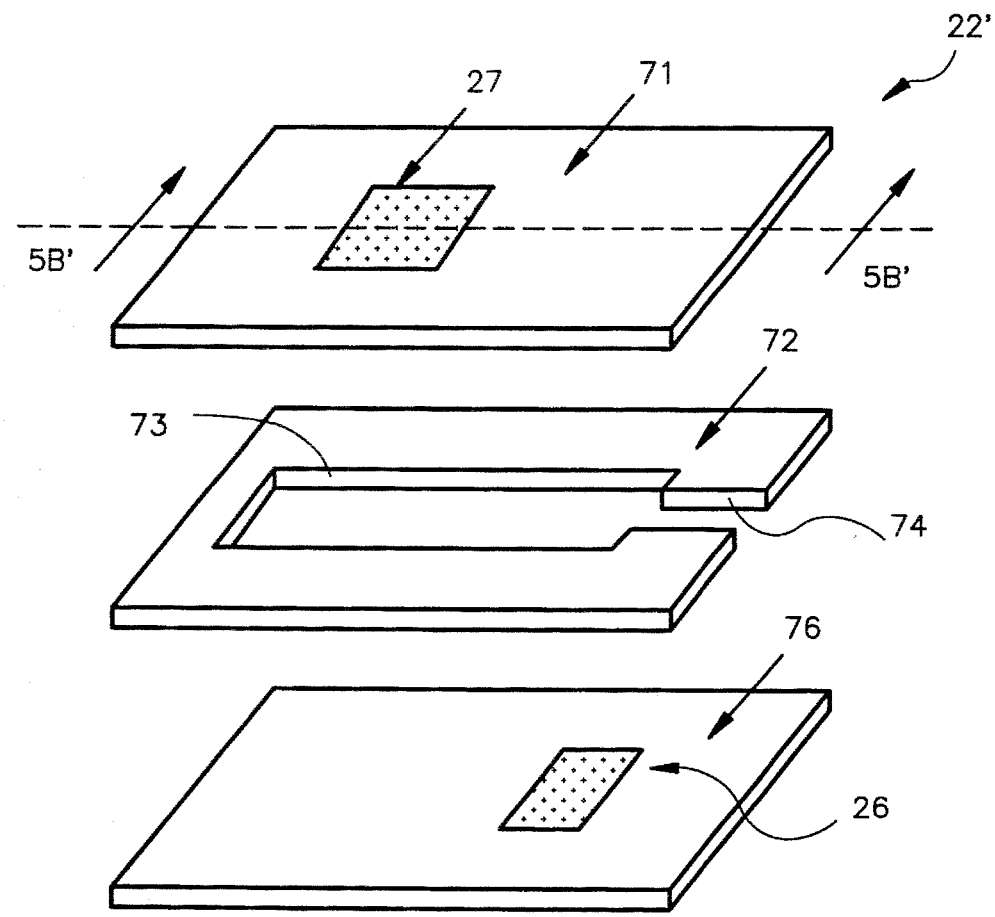
FIG. 5A shows an assembly view and FIG. 5B shows a cross sectional view taken along line 5B'—5B'.
Figure 5B:
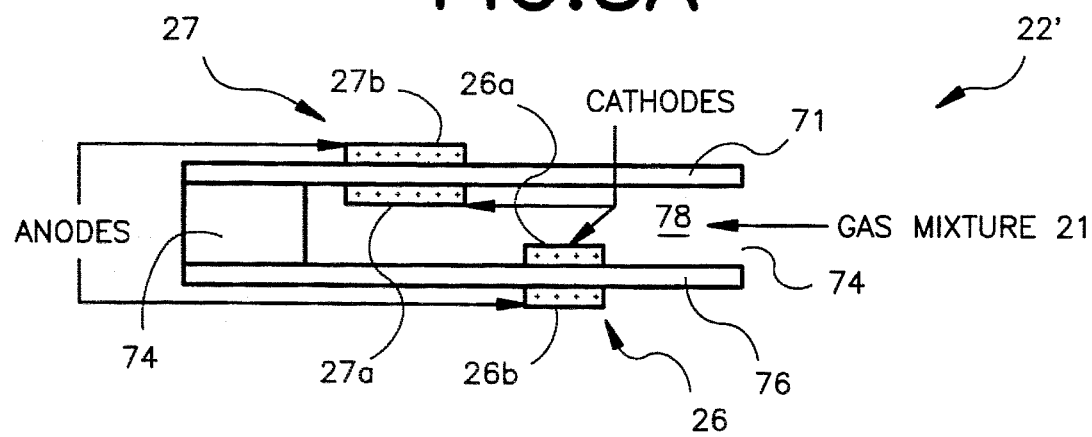

The physical structure of the $NO_x$ sensor 22 can exhibit many possible configurations. As an example, the $NO_x$ sensor 22 could be designed as shown in FIGS. 5A and 5B. FIGS. 5A and 5B illustrate a first embodiment, denoted as reference numeral 22', having a single hole for ingress and egress of the gas mixture 21. The $NO_x$ sensor 22' has (a) a planar, first YSZ electrolyte layer 71, (b) a C-shaped alumina insulating layer 72 with an internal aperture 73 and a hole 74 connecting the aperture 73 to the outer edge of the alumina insulating layer 72, and (c) a planar, second YSZ electrolyte layer 76. Together, these layers form a single hole structure, as shown in FIG. 5b, having an internal chamber 78 with inlet 74.

The $O_2$ pumping cell 26 (optional; not necessary) can be established at the second YSZ electrolyte layer 76, and the $NO_x$ sensing cell 27 is established at the first YSZ electrolyte layer 71. Further, each cell 26 and 27 has a pair of electrocatalysts 26a, 26b and 27a, 27b, respectively. Electrocatalysts 26a, 27a, which are situated within the internal cavity 78 (FIG. 5B), serve as cathodes for their respective cells, and the external electrocatalysts 26b, 27b, serve as anodes for their respective cells.

In operation, the gas mixture 21 enters the hole 74. The $O_2$ within the gas mixture 21 decomposes on the internal cathode electrocatalyst 26a, if present, and oxygen ions $O_2$. pass through the second YSZ electrolyte layer 76 to the external anode electrocatalyst 26b. The decomposition of the $O_2$ gas and the driving force of the ion transfer is caused by the pumping cell voltage bias $V_{bp}$.

The $NO_x$ sensing cell 27, which is situated farther in the cavity 78 from the hole 74 than the optional $O_2$ pumping cell 26, consumes $NO_x$ in the gas mixture 21. The $NO_x$ gas decomposes on the cathode electrocatalyst 27a, and the resultant ions $O^{2-}$ are transferred from the internal cathode electrocatalyst 27a to the external anode electrocatalyst 27b. The ion transfer results in the current $i_s$ which is measured by the DPV mechanism 28.

As another example of a possible structure for the $NO_x$ sensor 22, FIGS. 6A and 6B show a second embodiment, denoted generally as reference 22", having a single-cell for sensing $NO_x$ concentration. As shown, a porous YSZ layer 81 acts as both a gas diffusion barrier and an electrolyte for the sensing cell 27. Further, the sensing cell 27 has a cathode electrocatalyst 83a situated between the porous YSZ electrolyte/barrier layer 81 and the substrate 82, and an anode electrocatalyst 83b situated on the opposing side of the YSZ electrolyte/barrier layer 81. Further, an alumina insulating layer 84 permits easier electrical connection to the cathode electrocatalyst 83a near the end of the structure.

A third embodiment of the $NO_x$ sensor 22 is shown in FIGS. 7A and 7B, and generally delineated by reference numeral 22'''. The $NO_x$ sensor 22''' has both an $O_2$ pumping cell 26 and an $NO_x$ sensing cell 27. In the double-cell porous-type $NO_x$ sensor 22''' of the third embodiment, a porous YSZ layer 86 is used as both a gas diffusion barrier and an electrolyte for the $O_2$ pumping cell 26. The $NO_x$ sensor 22''' is situated about a substrate 87. The $O_2$ pumping cell 26 is made up of the electrolyte YSZ layer 86, the cathode electrocatalyst 88a, and the anode electrocatalyst 88b. Moreover, the $NO_x$ sensing cell 27 is made up of the electrolyte substrate 87, the cathode electrocatalyst 89a, and the anode electrocatalyst 89b. An alumina insulating layer 91 is disposed between the YSZ layer 86 and the cathode electrocatalyst 88a of the $O_2$ pumping cell 26 so that the $O_2$ pumping cell 26 effectively removes oxygen associated with the $NO_x$ sensing cell 27. Further, a porous layer 92, preferably alumina, is disposed between the YSZ layer 86 and the cathode electrocatalyst 89a of the $NO_x$ sensing cell 27 in order to permit passage of the gas mixture 21 to the cathode electrocatalyst 89a. Finally, an alumina insulating layer 93 is disposed between the cathode electrocatalyst 88a of the $O_2$ pumping cell 26 and the electrolyte substrate 87 in order to isolate the cells 26, 27.

EXPERIMENT

1. Overview

Operation parameters of DPV, two metal electrocatalysts (i.e., Au and Pt), and configurations of a gas-diffusion-limiting mode $NO_x$ sensor 22 (i.e., single-hole-type and porous-type) were selected for determining the feasibility of the DPV $NO_x$ sensor system 20 (FIG. 1). Sensors 22 were fabricated having multilayers of ceramics (i.e., alumina and YSZ) and metals (i.e., Au and Pt), which are suitable for cyclic voltammetry (CV) and DPV experiments. Prior to the DPV experiment, a CV experiment was conducted to evaluate the metal electrocatalysts. It was determined that the Au electrocatalyst discriminated between the reductions of $O_2$ and $NO_x$: the onset of the reduction of $O_2$ occurred at low voltage (0 to 0.3 V), and that of $NO_x$ occurred at high voltage (0.9 to 1.1 V). The DPV experiment was conducted with the same $NO_x$ sensor 22 having the Au electrocatalyst in the varying $NO_x$ concentrations in the presence of 0.5% $O_2$ and 5% $O_2$. The sensitivity of the $NO_x$ measurement greatly increased in DPV compared to CV as the effect of coexisting $O_2$ was eliminated.

To determine whether or not the sensitivity could be further improved, the DPV measurements were carried out on an $NO_x$ sensor 22, originally single-celled (FIG. 6), modified by addition of an $O_2$ pumping cell 26 (FIG. 7) in order to reduce the background $O_2$ concentration by electrochemically pumping out $O_2$. The results were as good as those of the case without the $O_2$ pumping cell.

2. Test Setup

The data acquisition system 23 (FIG. 1) was implemented with a Apple Macintosh computer and its peripherals. The computer acquired and processed the data for CV and DPV. The voltage sweeping rate (i.e., from 0 to 2 V) for the voltage pulse $v_{pulse}$ could vary from 2 mV/s to 0.8 V/s, but the pulse times could be no shorter than 30 ms. The pulse time was limited by the Macintosh clocking speed. The Macintosh tick counter provided 60 ticks/s, resulting in a pulse width for the pulse $v_{pulse}$ of about 17 ms. Considering the overhead of both sending and receiving data from the system 23, a practical limit was 30-ms pulses $v_{pulse}$. Smoothing, to remove noise, was carried out by the averaging of three to five values. Voltage and current waveforms of the DPV are given in FIG. 4.

Materials for fabricating $NO_x$ sensors 22 were purchased, including sealing glass and Au paste. Three different $NO_x$ concentrations—2% (20,000 ppm), 2000 ppm, and 200 ppm balanced by NZ—and 1% $O_2$ balanced $N_2$ were also purchased. ($NO_x$ consists of NO and $NO_2$, but as NO comprises most of the emitting $NO_x$ in the exhaust, the $NO_x$ detection was focused on.)

2.1 Theoretical Evaluation of the Feasibility of an Amperometric $NO_x$ Sensor

2.1.1 Electrocatalysts

Au and Pt were selected and evaluated as electrocatalysts for the reduction of $O_2$ and $NO_x$ because the two metals have different characteristics in reducing $O_2$ at high temperatures. Pt is a very good electrocatalyst for $O_2$ reduction. It is most frequently used as an electrocatalyst of an $O_2$ sensor. However, Au is generally known to be an ineffective electrocatalyst for the reduction of $O_2$ (at least in the Au/YSZ system). It is believed that either the adsorption, or transport kinetics, or both, of $O_2$ are not very favorable on the Au surface.

For the reduction of $NO_x$ on Pt, literature sources-although in considerable disagreement about the proposed mechanisms-generally agree that the reduction kinetics are slow. It has also been reported that the $NO_x$ decomposition rate is inversely dependent upon the $O_2$ partial pressure, which indicates the inhibiting role of $O_2$.

In the source-limiting mode of operation, the $O_2$ pressure on the cathode electrocatalyst decreases with an increase of applied voltage bias $V_b$. If the $NO_x$ sensor 22 operates in a gas mixture 21 of $O_2$ and $NO_x$, the onset of $NO_x$ reduction should occur at a high voltage where the $O_2$ pressure is low enough to diminish the inhibiting role of $O_2$. Au, known to be a slow electrocatalyst, will further separate the potentials at which reduction occurs for $O_2$ and $NO_x$. Therefore, Au was selected as the electrocatalyst for the DPV experiment, but Pt was also used to compare the DPV results.

Existing electrocatalysts were utilized without optimization. The two metals were prepared by RF sputtering.

2.1.2 DPV for Sensitive and Selective Detection of $NO_x$

In DPV, as previously discussed, a small voltage pulse $v_{pulse}$ is periodically superimposed on the sensing cell bias $V_{bs}$ (reference numeral 61a in FIG. 4). The DPV signal (reference numeral 61d in FIG. 4) can be produced by the difference of the two currents, one current (reference numeral 61b in FIG. 4 sampled just before the pulse and another current (reference numeral 61c in FIG. 4) sampled during the pulse.

The observed current relaxation shown in FIG. 4 at reference numeral 61d primarily comes from two different physical origins: capacitive (reference numeral 61b in FIG. 4) and mass transport (reference numeral 61c in FIG. 4). The capacitive part is due to the rearrangement of the double layer at the electrocatalyst/electrolyte interface. In the solution electrochemical system, the relaxation time associated with the interface capacitance usually does not exceed 3 ms. The relaxation has an exponential relation with respect to time.

The relaxation related to the mass transport is actually due to the depletion (or purging) of gases in the depletion layer on the electrocatalyst. The current decays inversely as $t^{1/2}$. The depletion layer, formed during a pulse $v_{pulse}$, is filled with the measuring gas (i.e., $NO_x$) for the rest time following the pulse $v_{pulse}$, so the relaxation of the Faradaic current during the pulse $v_{pulse}$ is repeated at every pulse application. The magnitude of the relaxed Faradaic current is related to the gas concentration.

As the current subtraction in DPV yields a signal 61d that resembles the derivative of the conventional CV signals, the background current due to the coexisting gases can be eliminated in DPV operation. The DPV readout also eliminates most of the capacitive charging current and provides a significantly better signal-to-background ratio. The width and magnitude of the pulse $v_{pulse}$ should be adjusted to completely eliminate the capacitive current. The subtraction also eliminates the effect of drift on the measurement.

DPV's selectivity and resolution would be increased if the reduction reactions of coexisting gases occur at different potentials. This can be accomplished by the use of a proper electrocatalyst, which, for example, discriminates between the reduction of $NO_x$ and $O_2$.

In summary, DPV has three inherent advantages over CV: (a) DPV sensitivity is several orders of magnitude better than CV; (b) DPV selectivity is at least 10 to 20 times better than selectivity obtained with conventional CV; and (c) DPV drift is negligible.

2.1.3 Sensor Structure

In a conventional solution electrochemical system, the depletion layer in front of the electrocatalyst naturally forms during the CV operation because of the slow diffusion of species in the liquid medium. In the gas phase, a rather rough, thick electrocatalyst can be sufficient. As was mentioned earlier, existing electrocatalysts (i.e., Au and Pt) were used in this experiment and each electrocatalyst was prepared by conventional RF sputtering.

Several $NO_x$ sensors 22 having a gas-diffusion-limiting barrier were examined for our exploration of the feasibility of the $NO_x$ sensor 22. One species of design is the single-hole-type $NO_x$ sensor 22' (FIG. 5) and the other is the porous-type $NO_x$ sensors 22", 22''' (single-cell of FIGS. 6; double-cell of FIG. 7). FIG. 5 shows exploded and cross-sectional views of the single-hole-type $NO_x$ sensor 22'. FIGS. 6A and 6B show top and cross-sectional views, respectively, of the porous-type $NO_x$ sensor 22" having a single $NO_x$ sensing cell. FIGS. 7A and 7B show top and cross-sectional views, respectively, of the porous-type $NO_x$ sensor 22''' having an $NO_x$ sensing cell and an $O_2$ pumping cell.

In the single-hole-type $NO_x$ sensor 22', the $O_2$ pumping cell 26 near the opening of the gas-diffusion-limiting hole 74 decreases the $O_2$ pressure in the hole, and the $NO_x$ sensing cell 27 conducts the DPV experiment. The advantage of this configuration is the accurate design of the sensor geometry-that is, the hole diameter and length and electrocatalyst area. However, its fabrication may require the optimization of a number of processes. The bonding of the three ceramic layers (i.e., an alumina and two YSZ) without damaging the metal electrocatalyst is an especially challenging process.

In the porous-type $NO_x$ sensors 22', 22''', the porous YSZ layers 81 (FIGS. 6A, 6B), 86 (FIGS. 7A, 7B) act as both a gas-diffusion barrier and an electrolyte for a cell. The advantage of this design is easy fabrication of the structure. The porous layer 81, 86 can accommodate thermal strain to a certain level without mechanical failure.

2.1.4 Material Compatibility

The major parts of the $NO_x$ sensors 22 are YSZ, alumina as an insulator, and the metal electrocatalyst (i.e., Au and Pt). Chemical and thermal compatibilities among the layers were examined to confirm that the multilayered $NO_x$ sensor 22 could be tested at high temperatures without failure.

Dense YSZ coupon was selected as a substrate for the porous-type $NO_x$ sensors 22', 22'''. Alumina was selected as an insulating layer between YSZ and Pt (or Au). Thermal expansion of alumina is approximately 10% less than that of YSZ, but the porous alumina (formed by the plasma spray coating) can accommodate the thermal strain produced by the thermal expansion mismatch between YSZ and alumina.

Corning #1415 barium borosilicate glass was selected as a sealer for bonding the alumina and zirconia layers of the single-hole-type $NO_x$ sensor 22'. Its thermal expansion coefficient is $96.7 \times 10^{-7}$ which is between alumina's and YSZ's thermal expansion coefficients. The softening temperature of the glass is 766° C., which is sufficient for the amperometric-type sensor operation.

Au paste was used to fill the gap between the two ceramic pieces and to provide electric lead continuity.

2.2. Demonstration of the Feasibility of the DPV $NO_x$ Sensor System 2.2.1 Sensor Fabrication The $NO_x$ sensors 22', 22", 22''' were fabricated. The single-hole-type $NO_x$ sensor 22' was fabricated using YSZ and alumina green tapes. The green tapes were cut to form an appropriate shape, as shown in FIG. 5, and fired at 1550° C. in air. The Au electrocatalysts 26a, 26b, 27a, 27b were coated on the fired YSZ by RF sputtering, and then Au paste was coated on the thin-film Au for electric continuity. Electric leads from the electrocatalysts to the outer surface of the $NO_x$ sensor 22' were made by coating Au paste on the fired ceramic layers. The $NO_x$ sensors 22' were completed by gluing the ceramic layers with the sealing glass.

The $O_2$ in the chamber 78 was electrochemically pumped out by the electrolyte pumping cell 26 near the opening of the gas-diffusion-limiting hole 74, while the $O_2$ pressure in the chamber 78 was measured by the $NO_x$ sensing cell 27. The maximum EMF observed was approximately 40 mV, which means that the $O_2$ concentration on the measuring electrocatalyst 27a in the cavity is approximately one order of magnitude lower than in the test gas. The measured concentration is higher than expected. This is attributed to either ineffective pumping capacity, or gas leaking through cracks in the sealing glass, or both. Resolving the problem required gas-tight sealing of the ceramic layers, and decreasing the intake of the gas by reducing the cross-sectional area of the gas-diffusion-limiting hole 74. Because of the complexity of the sample fabrication, porous-type $NO_x$ sensors 22' were used for both the CV and DPV experiments.

Porous-type $NO_x$ sensors 22", 22''' (FIGS. 6, 7) were made primarily by using plasma spray and RF sputtering techniques. Ceramic layers such as alumina and YSZ were coated by the plasma spray method, while the Au and Pt electrocatalysts 83a, 83b 88a, 88b, 89a, 89b were coated by RF sputtering. Masking techniques were used to selectively coat the foregoing layers. Layer thicknesses were as follows: YSZ electrolytes of about 150 to 200 μm, an alumina dielectric of about 10 to 20 μm, and an Au or Pt electrocatalyst of about 0.4 to 0.7 μm.

The composite electrocatalyst Au/Pt was made by alternating the coating of very thin Au and Pt (each layer approximately 200 to 400 angstroms).

The YSZ film actually acts as both a gas diffusion barrier and an $O_2$ ion-conducting electrolyte. Plasma-sprayed YSZ films are strongly bonded to the substrates and have exceptionally high integrity because YSZ powder is melted in a high-temperature gas plasma and propelled onto the substrate during deposition. However, its ionic conductivity is not as high as that of YSZ electrolytes sintered at high temperatures, as the films are not very dense. Because almost fully activated YSZ films can be obtained by the plasma spray method without excessive heating of the substrate already carrying the thin-film Pt electrocatalyst, the plasma spray method is very suitable for fabricating the multilayered $NO_x$ sensors 22 containing the ceramic materials and thin film metal electrocatalysts on various substrates.

The area of the internal electrocatalyst 83b (FIG. 6) was approximately 5 mm×5 mm, which produced the limiting current of 1 to 3 mA in 0.5% $O_2$ at about 740° C. Note that the limiting current is proportional to the area of the electrocatalyst and inversely proportional to the thickness of the gas-diffusion limiting layer 81.

2.2.2 CV Experiment and Electrocatalyst Evaluation

Experiments using conventional CV were conducted on the double-cell porous-type $NO_x$ sensor 22''' (FIG. 7) having different electrocatalysts (i.e., Pt, Au, and multilayered composite electrocatalysts Pt/Au) at about 740° C. To vary the $NO_x$ and $O_2$ concentrations, 2% $NO_x$, 1% $O_2$, and $N_2$ were mixed. The total flow rate varied from 1000 to 1500 sccm. CV measurements were carried out using a potentiometer (BAR CV27). Scanning rate was 40 mV/s, but 80 and 400 mV/s were tried to analyze the effect of scanning rate on the measurement. Data was recorded on an X-Y plotter and sent to the data acquisition system 23 (FIG. 1) for further analysis.

Figure 8:
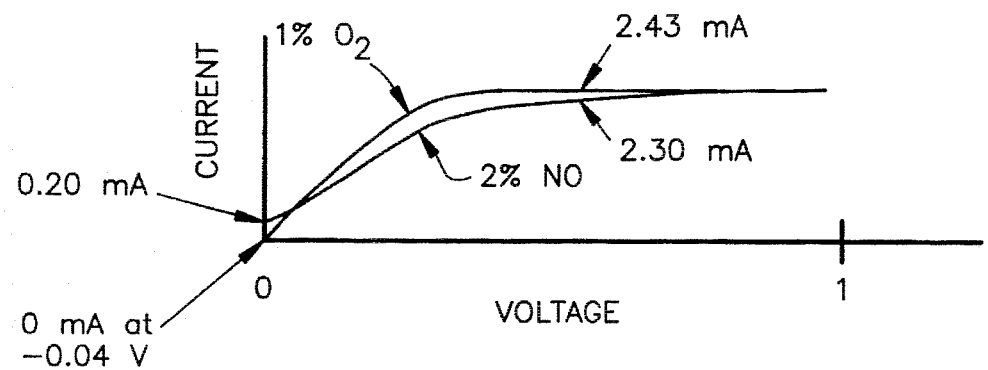
FIG. 8 shows a graph of current versus voltage characteristics of the double-cell porous-type $NO_x$ sensor of FIG. 7 having a Pt electrocatalyst in a gas mixture having about 2% $NO_x$, 1% $O_2$ at about 740° C.
Figure 9:
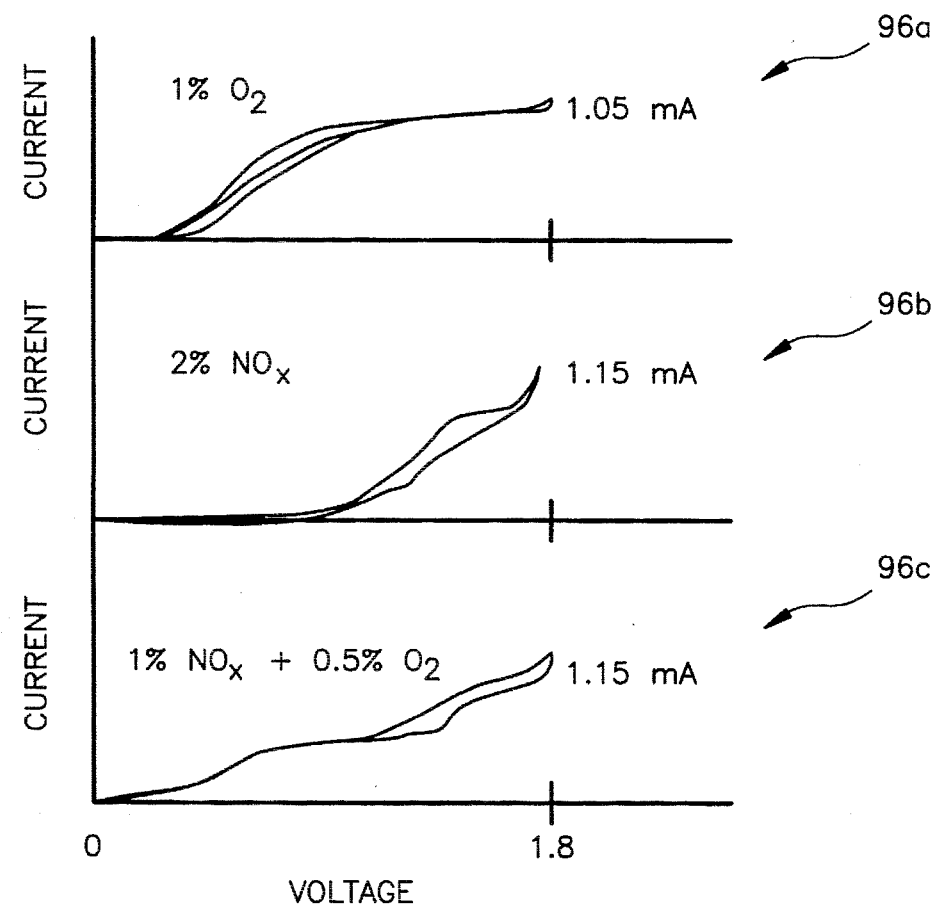
FIG. 9 shows a graph of current versus voltage characteristics of the double-cell porous-type $NO_x$ sensor of FIG. 7 having an Au electrocatalyst in a gas mixture having about 2% $NO_x$, 1% $O_2$, and 0.5% $O_2$ +1% $NO_x$ at about 740° C.
Figure 10:
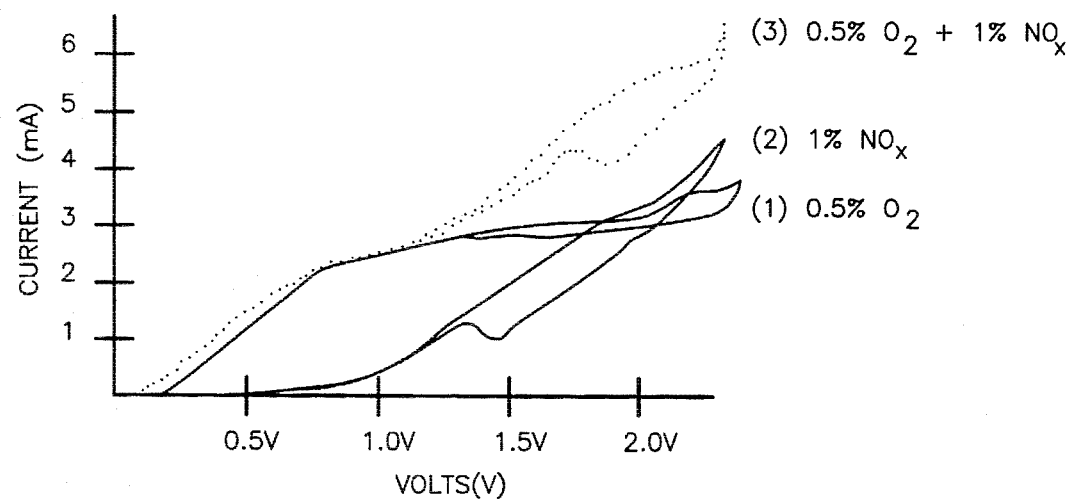
FIG. 10 shows a graph of current versus voltage characteristics of the double-cell porous-type $NO_x$ sensor of FIG. 7 having a Pt/Au composite electrocatalyst in a gas mixture having about 0.5% $O_2$, 1% $NO_x$, and about 0.5% $O_2$+1% $NO_x$ at approximately 740° C.

The test results of the $NO_x$ sensor 22''' having Pt, Au, and the Pt/Au composite are shown in FIGS. 8 through 10. Reductions of $O_2$ and $NO_x$ occur on the Pt electrocatalyst from zero potential, as shown in FIG. 8. FIG. 8 shows current versus voltage characteristics of the porous-type $NO_x$ sensor 22''' having Pt electrocatalyst in 2% $NO_x$, 1% $O_2$ at about 740° C. Current flow at zero potential was observed on the Pt electrocatalyst. It is attributed to the chemical reaction of $NO_x$ on Pt electrocatalyst; $NO_x$ is decomposed to $N_2$ and $O_2$ to increase the $O_2$ concentration, which causes the current flow at zero potential. Because the slopes of the $NO_x$ and $O_2$ reduction curves on the Pt electrocatalyst are different, it is still possible, using DPV, to discriminate between the two gases.

As shown in FIG. 9, the onset of reduction of $NO_x$ and $O_2$ on the Au electrocatalyst occurs at different voltages. FIG. 9 shows current versus voltage characteristics of the porous-type $NO_x$ sensor 22''' having Au electrocatalyst in 2% $NO_x$, 1% $O_2$, and 0.5% $O_2$+1% $NO_x$ at about 740° C. The reduction of $NO_x$ occurs between 0.9 and 1.1 V with respect to the counter electrocatalyst, while the reduction of $O_2$ occurs at approximately 0.3 V. When the $NO_x$ sensor 22''' is operated in the mixture 21 of $NO_x$ and $O_2$, the measured current curve resembles the superimposition of the two curves shown for each gas (reference numeral 96c of FIG. 9). The slope of the curve increases at approximately 0.9 to 1.1 V because of the reduction of $NO_x$. The observed behavior is primarily due to the different kinetics of $O_2$ and $NO_x$ on the Au electrocatalysts; on the Pt electrocatalyst, the reduction of $NO_x$ is as fast as that of $O_2$, but on the Au electrocatalyst, the reduction of $NO_x$ is more sluggish than that of $O_2$.

The Au/Pt composite was tested to explore the feasibility of tailoring the electrocatalyst material. FIG. 10 illustrates the test results. FIG. 10 shows current versus voltage characteristics of the porous-type $NO_x$ sensor 22''' (FIG. 7) having Pt/Au composite electrocatalyst in about 0.5% $O_2$, 1% $NO_x$, and 0.5% $O_2$+1% $NO_x$ at about 740° C. The reduction of $O_2$ starts near the zero voltage, similar to the reaction on the Pt electrocatalyst, but the onset voltage of $NO_x$ reduction still requires a rather high potential, similar to the reaction on the Au electrocatalyst. A close look at the $NO_x$ reduction curve reveals a shift to a lower onset voltage compared to that of the Au electrocatalyst. The materials-tailoring concept is feasible, but further study is required to optimize the process.

In the CV measurement with the present electrocatalyst and sensor configuration, the hysteresis loop in the current-voltage curve became wider with an increase in the scanning rate, but any characteristic peak associated with $O_2$ or $NO_x$ did not appear. However, in the DPV measurement carried out on the same sample, the distinct peaks representing $O_2$ and $NO_x$ were produced.

2.2.3 DPV with Single-Cell Porous-Type Sensor 22"

Figure 11:
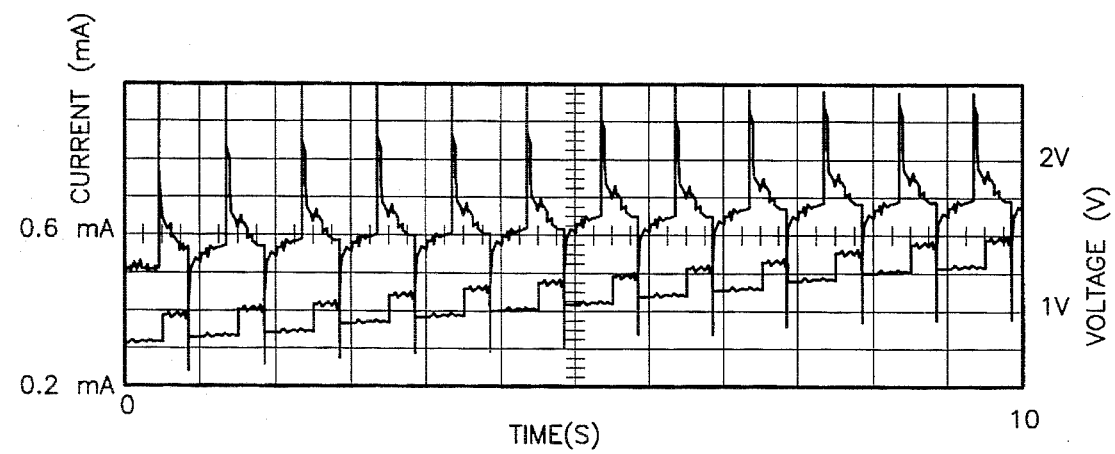
FIG. 11 shows an oscilloscope screen of current relaxation behavior of the single-cell porous-type $NO_x$ sensor of FIG. 6 having an Au electrocatalyst responding to a voltage pulse $v_{pulse}$.

A conventional oscilloscope was used to analyze the current relaxation behavior of the single-cell porous-type $NO_x$ sensor 22" (FIG. 6) responding to the voltage pulse of DPV. The parameters of DPV were determined based on the results. An example of the current relaxation is given in FIG. 11. FIG. 11 shows current relaxation behavior of the porous-type $NO_x$ sensor 22" having Au electrocatalyst, responding to voltage pulse. As was discussed, the relaxing current consists of two components: capacitive and mass transport. Application of a pulse results in a current spike due to the charging of the double layer. The charging spike rapidly decays in a few milliseconds; this is followed by a slow decrease in current, indicating diffusion-controlled Faradaic current. The current-time behavior shows the $t^{-1/2}$ relation. When the pulse application was stopped, a negative current spike appeared and decayed to zero. The relation time depends on the magnitude of voltage, sweeping speed, and gas concentration, but generally it was at least 200 to 300 ms until the relaxation was completed.

As was described previously, the sampling interval of the present data acquisition system 23 is unfortunately limited to 30 ms. With the data acquisition system 23 in the specific embodiment described herein, it is difficult to measure the diffusion-controlled Faradaic current 61c (FIG. 4), which immediately follows the charging spike appearing for a few milliseconds, in an accurate and consistent manner. For the consistent DPV measurement in this phase, a pulse width of approximately 400 ms and a rest time of 600 ms were used. A pulse height of about 150 mV was used as an optimum performance of DPV technique. The sweeping speed was about 0.05 sec; it thus takes 40 s to sweep from 0 to 2 V. Under these conditions, the diffusion-controlled Faradaic current almost completely decays. This means that DPV sensitivity and resolution would not be fully maximized, but the present DPV still takes advantage of the subtraction process.

DPV experiments were carried out on single-cell porous-type $NO_x$ sensor 22" (FIG. 6) samples at about 740° C. Three different $NO_x$ concentrations—(a) 2%, (b) 2000 ppm, and (c) 200 ppm—were mixed with about 1% $O_2$ and $N_2$ to vary the $NO_x$ concentration from a few ppm to about 1%. $O_2$ concentration was maintained at about 0.5% and about 5%.

2.2.4 Gold (Au) Electrocatalyst

Figure 12A:
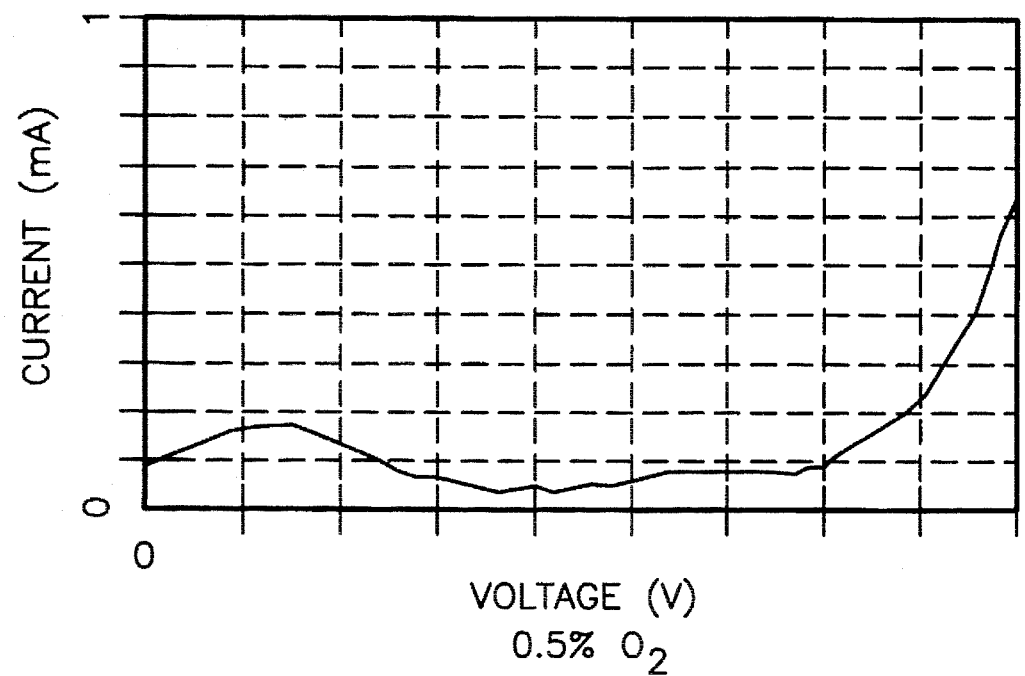
FIGS. 12A–12D show graphs of current versus voltage characteristics of DPV measurements of the single-cell porous-type $NO_x$ sensor of FIG. 6 in various gas mixtures of $NO_x$ and $O_2$ at about 740° C.
Figure 12B:
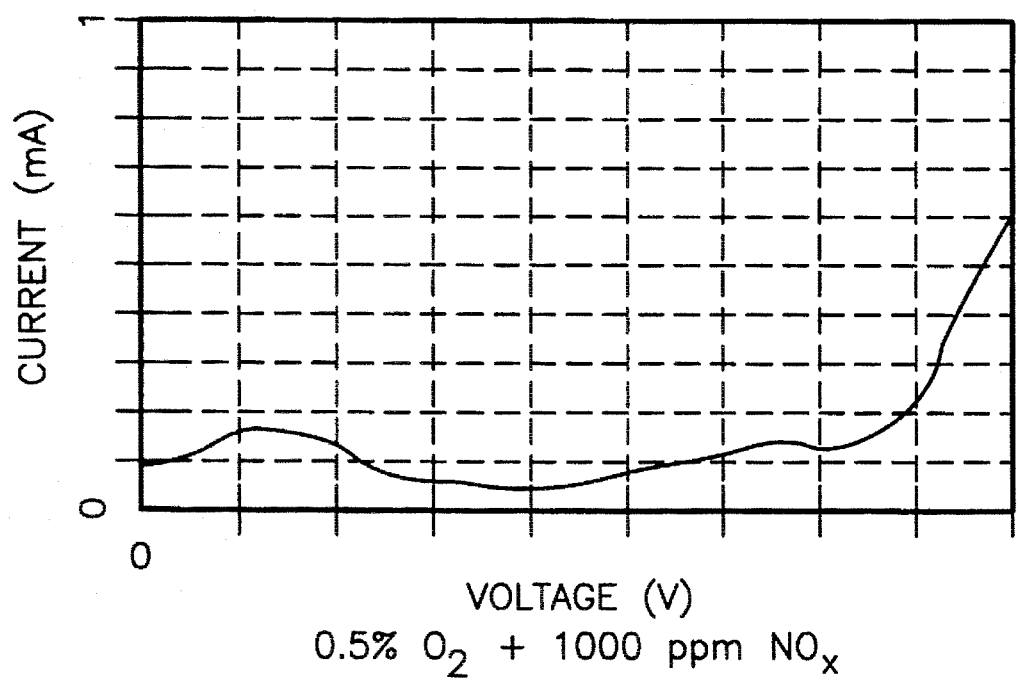
Figure 12C:
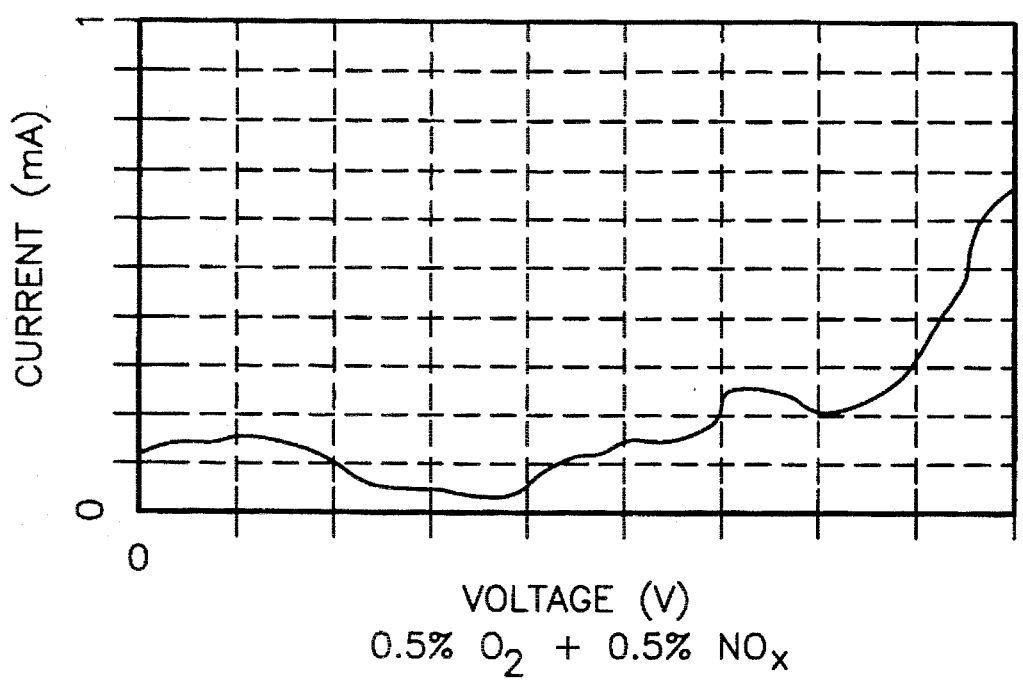
Figure 12D:
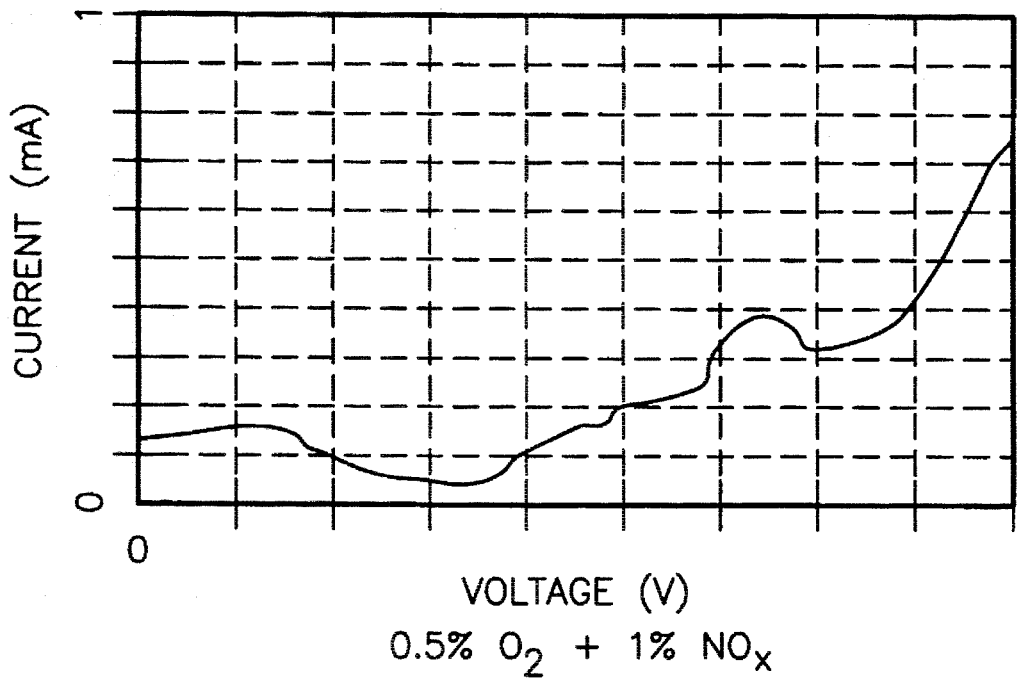

The results of DPV measurement on the $NO_x$ sensor 22" having the Au electrocatalyst are given in FIGS. 12A–12D. FIGS. 12A–12D show current versus voltage characteristics of DPV measurement in varying mixture 21s of $NO_x$ and $O_2$ at about 740° C. $O_2$ concentration was maintained at approximately 0.5%, and $NO_x$ concentration varied from about 0% to 1%. Compared to the flat response of conventional CV (FIG. 9), the DPV measurements as shown in FIGS. 12A–12D give a peaked (bump-shaped) output. The peak at around 0.25 V in these figures represents the current increase due $O_2$ reduction, and the peak near approximately 1.3 V (see FIG. 12C and 12D) represents the current increase due to $NO_x$ reduction. The current increase between about 1.6 V and about 1.8 V reflects the electronic leakage through the YSZ electrolyte 81 (FIG. 6), or the electrolyte decomposition. The background current appearing between about 0.6 V to about 1.4 V in FIG. 12A is caused by the current increase with voltage in the gas-diffusion-limited region. Ideally, the current should be zero if the current associated with the $O_2$ reduction would be saturated in the gas-diffusion-limiting mode operation. The source-limiting process may be more easily controlled by using a thick electrocatalyst.

The height of the peak near about 1.3 V associated with $NO_x$ is increased with $NO_x$ concentration. However, it is shown that the peak becomes broad with the increase of $NO_x$ concentration. Phenomenologically, this is due to the large cell resistance, as the slope of the current-voltage curve is determined by this resistance. If the resistance is reduced, the curve is steeper in the ohmic region, and the DPV peak should be sharper. It should be emphasized that the $NO_x$ sensor 22" can be optimized to decrease the resistance. This can be accomplished, for example, by improving the electrocatalyst 83b (FIG. 6).

Figure 13A:
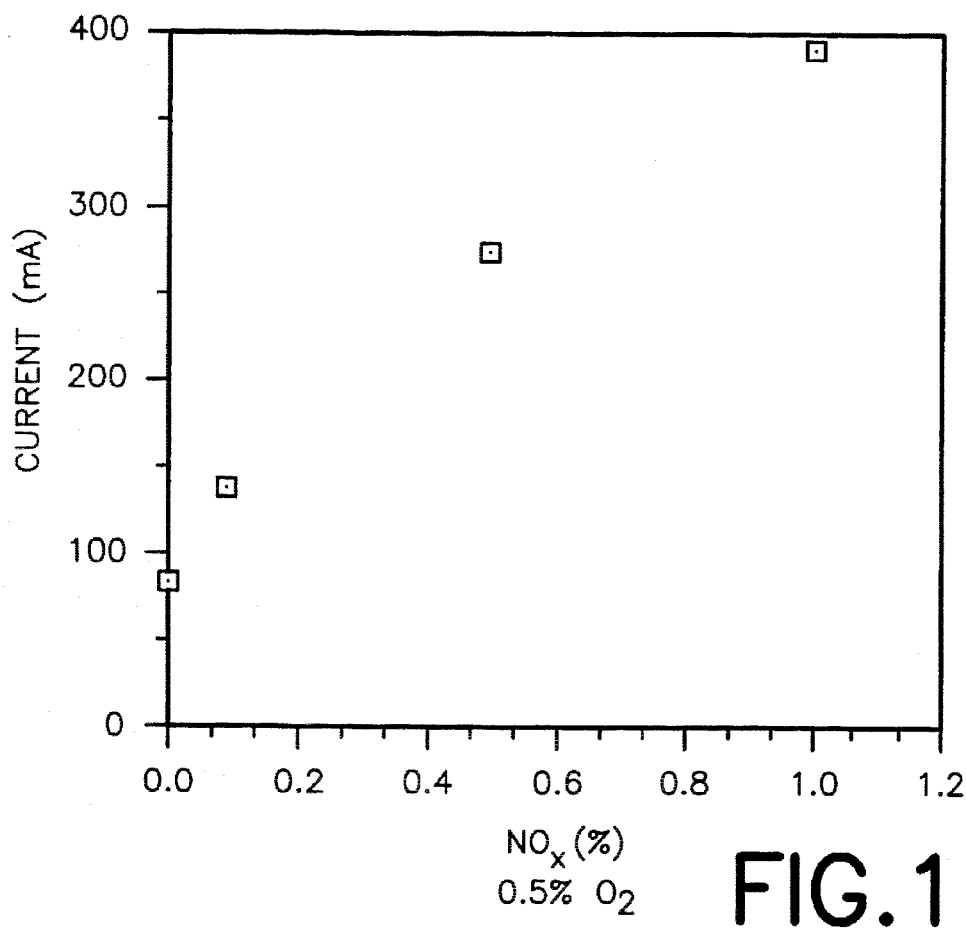
FIGS. 13A and 13B show graphs of current versus $NO_x$ concentration of DPV measurements of the single-cell porous-type $NO_x$ sensor of FIG. 6 in gas mixtures having $O_2$ at about 740° C.

The peak heights in FIG. 12 are plotted as a function of $NO_x$ concentration in FIG. 13A. As the $NO_x$ concentration increases, the measured current $i_s$ appears to be lower than the expected linear trend. If the peak area were plotted, it would be close to the linear relation. The present $NO_x$ sensor 22" has approximately 3 mm×3 mm electrocatalyst 83b (FIG. 6) and yields approximately 50 μA in the 1000-ppm $NO_x$. This corresponds to the current of approximately 0.5 μA in 10-ppm $NO_x$, which is large enough to electrochemically measure. If the electrocatalyst area is enlarged or if its coating is improved to yield a large current, the signal will be further increased.

Figure 13B:
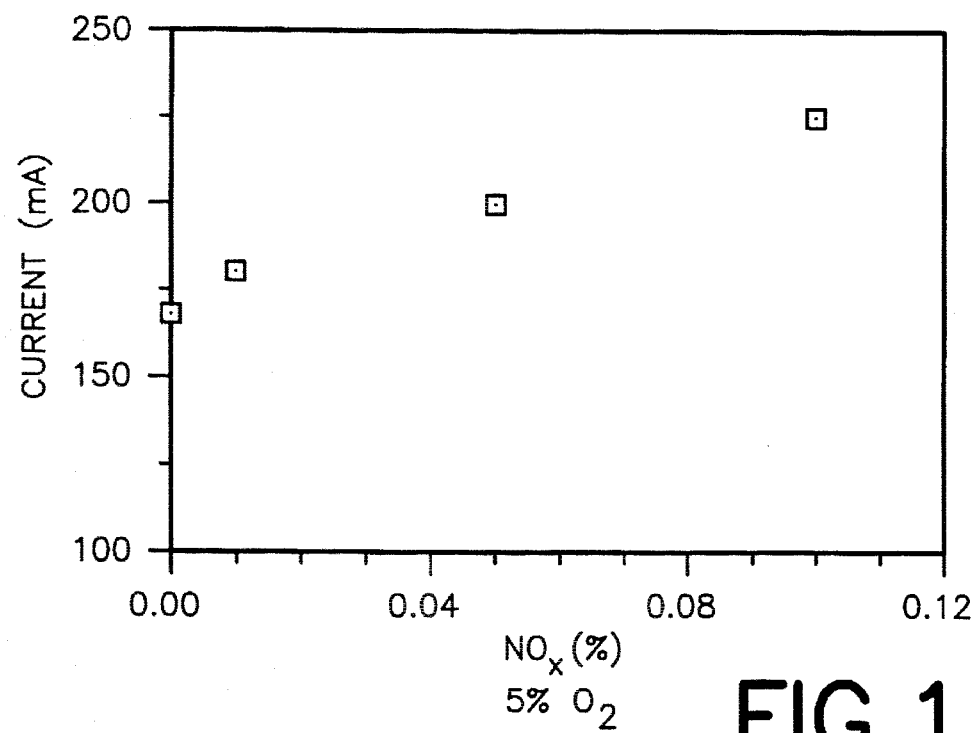

The results of the DPV measurement on the $NO_x$ sensor 22" in the presence of about 5% $O_2$ are presented in FIG. 13B. The current increase with respect to $NO_x$ concentration is almost the same in the range from 0% to 0.1% as that in the presence of 0.5% $O_2$. Even though the coexisting gas (i.e., $O_2$) is increased tenfold in concentration, the background current is not much affected. This result is due to the subtraction process of DPV.

2.2.5 Platinum (Pt) Electrocatalyst

The reduction of both $O_2$ and $NO_x$ occurs in the same voltage range (0 V to about 0.3 V), but the slopes of current-voltage curve are different (FIG. 8). Comparison of the DPV results indicated another peak associated with $NO_x$ reduction at approximately 0.25 V on the primary peak due to $O_2$ reduction. As the two peaks are superimposed, the method was not pursued.

2.2.6 DPV Experiment with Double-Cell Porous-Type Sensor 22''' in Reduced $O_2$ Concentration DPV experiments were conducted on the double-cell porous-type $NO_x$ sensor 22''' (FIG. 7) at about 740° C. Three different $NO_x$ concentrations-2%, 2000 ppm, and 200 ppm- were mixed with about 1% $O_2$ and $N_2$ to vary the $NO_x$ concentration from a few ppm to about 1%. The $O_2$ pumping cell 26 (88a, 86, 88b in FIG. 7B) electrochemically pumps out $O_2$ at the cathode electrocatalyst 88a, and the reduced $O_2$ concentration is monitored by the sensing cell 27 (89a, 87, 89b in FIG. 7B). As the $O_2$ concentration in the test gas is known, the measured EMF can be converted to the $O_2$ concentration between the pumping and sensing cells. By scanning the potential of the pumping cell from about 0 to 2 volts, a look-up table was made showing the $O_2$ concentration in the sensing cell associated with the pumping cell potential. The DPV experiment was conducted by the measuring the pumping cell 26, while the $O_2$ concentration in the sensing cell was maintained at a predetermined value (i.e., approx. 1.5 V) by selectively pumping out $O_2$. DPV measurements were carried out at the two different $O_2$ pressures—about 0.5% and about 5%.

Figure 14A:
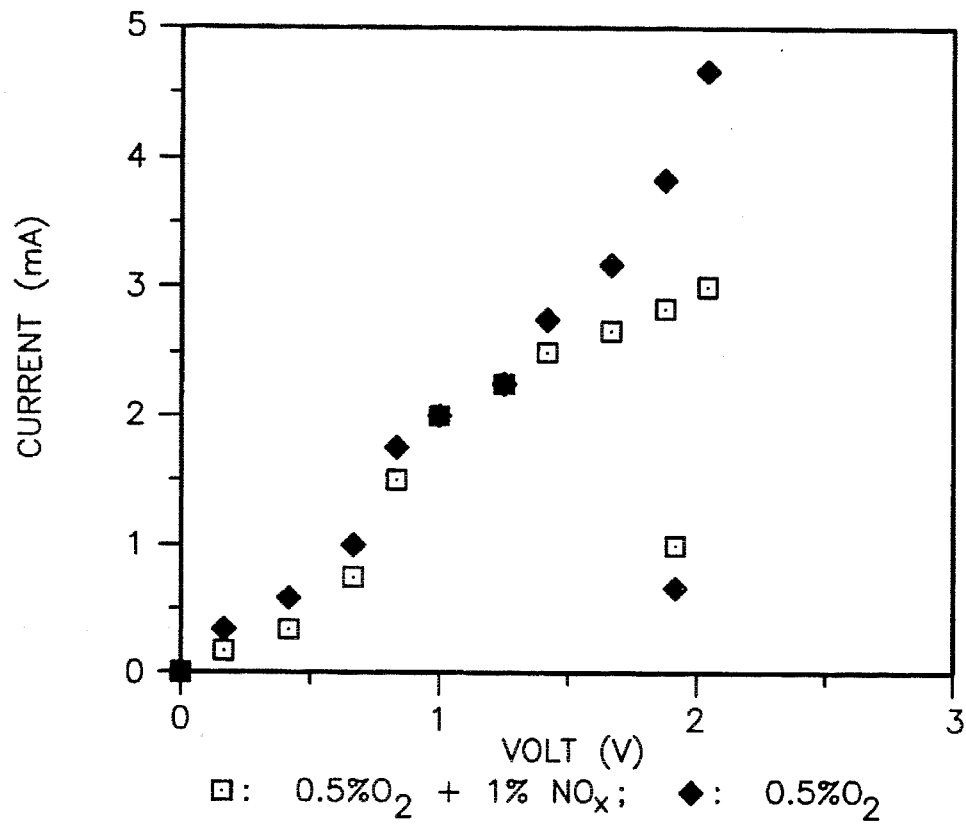
FIGS. 14A and 14B show graphs of reductions of oxygen pressure in the sensing cell of the double-cell porous-type DPV $NO_x$ sensor of FIG. 7 by electrochemically pumping out $O_2$ selectively with an $O_2$ pumping cell.
Figure 14B:
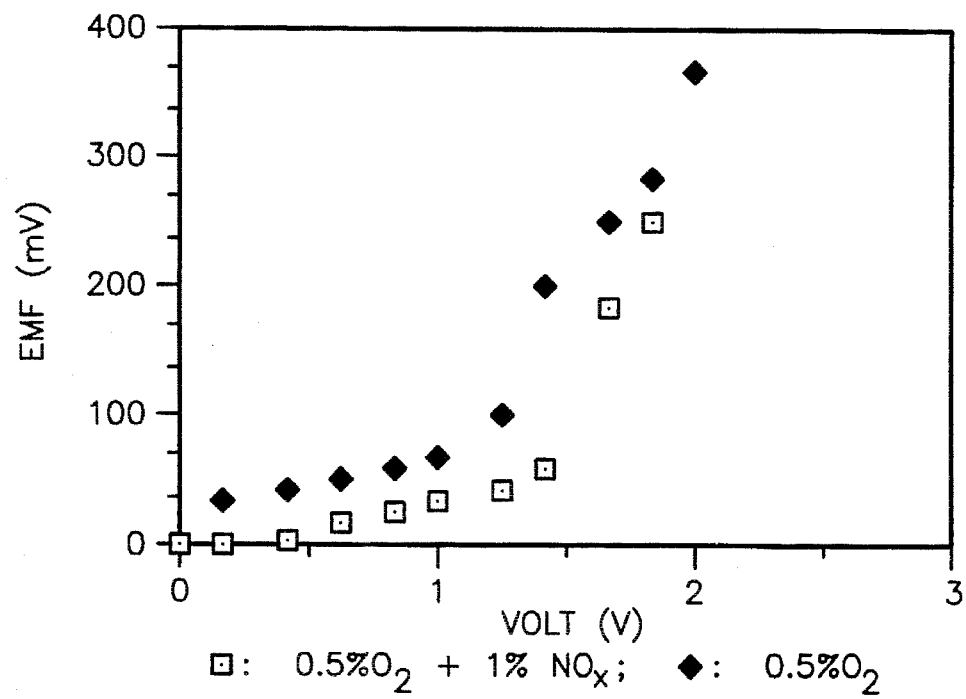

The results of the regulation of $O_2$ concentration are given in FIGS. 14A and 14B. Specifically, FIG. 14A shows the current versus voltage behavior of the pumping cell 26 and particularly the reduction of $O_2$ pressure in the sensing cell 27 by electrochemically pumping out $O_2$ selectively with the pumping cell 26. The corresponding $O_2$ pressure in the sensing cell 27 is presented in FIG. 14B. The $O_2$ pressure noticeably decreases at the beginning of the gas-diffusion-limiting region (i.e., about 1.3 V). An electromotive force (EMF) of approximately 50 mV is equivalent to the tenfold $O_2$ pressure difference at about 740° C. The $O_2$ pressure difference is approximately two orders of magnitude at about 1.5 V, which reflects the $O_2$ concentration of about 50 ppm in the sensing cell as the $O_2$ concentration of the test gas is approximately 5000 ppm.

The results of DPV experiment are shown in FIGS. 15A–15C. FIGS. 15A–15C show current versus $NO_x$ concentration of DPV measurement in the presence of 0.5% $O_2$, with $O_2$ concentration reduced by the $O_2$ pumping cell 26. DPV currents measured at about 1.5 V (of sensing cell 27) were plotted with respect to $NO_x$ concentration. Deviations from the linear trend in FIGS. 15A–15C are mostly due to either the readout of peak height of current, or the gas-handling system purging the exhaust gas upward or both. The background current is comparable to that of the single-cell porous-type $NO_x$ sensor 22" shown in FIG. 13, which proves that the subtraction process of DPV alone actually eliminates the effect of coexisting gas on the signal-to-background ratio. According to the results, the double-cell porous-type $NO_x$ sensor 22''' (FIG. 7) does not have a significant advantage over the single-cell porous-type $NO_x$ sensor 22" (FIG. 6) as far as DPV is concerned. However, the double-cell porous-type $NO_x$ sensor 22''' is very useful when the electrocatalytic activity of the electrocatalyst is affected by the $O_2$ pressure. Electrocatalytic activity in the reduced $O_2$ concentration is easily evaluated by the double-cell porous-type $NO_x$ sensor 22'''.

3.0 Acheivements of the Present Invention 3.1 DPV Experiment With Single-Cell Porous-Type $NO_x$ sensor 22"

DPV can selectively monitor $NO_x$ in the presence of $O_2$ with high precision. The concentration of background $O_2$ does not significantly affect the $NO_x$ measurement because of the mathematical process associated with DPV of combining the first and second sample signals. With the specific setup in this experiment, the sensitivity of $NO_x$ detection down to a few hundred ppm could be obtained, but for this experiment, the sensitivity was limited by the data acquisition system 23 (FIG. 1). A better electrocatalyst may also be necessary to improve sensitivity. The measurement of a few ppm of $NO_x$ is assuredly feasible with an improved electrocatalyst and data acquisition system 23.

3.2 Electrocatalyst for Selective Detection of $NO_x$ in the Presence of $O_2$

Reduction of $O_2$ and $NO_x$ on the Pt electrocatalyst occurs from zero potential. However, when the Au electrocatalyst is used, the reduction of $NO_x$ occurs at high potential (approximately 0.9 to 1.1 V) with respect to the counter electrocatalyst, while the reduction of $O_2$ occurs at low potential (approximately 0.3 V). When Au and Pt form a composite Au/Pt, the onset voltage of $O_2$ reduction is lower than with Au alone, and the onset of $NO_x$ reduction appears to decrease.

3.3 Experiment Results

The combination of three components-DPV, Au electrocatalyst, and YSZ as the electrolyte material-has great promise in monitoring the low $NO_x$ concentration in the presence of $O_2$. At least three important achievements were made during this experiment: (a) it was demonstrated that DPV can be used to measure a small amount of $NO_x$ in the presence of a much larger amount of $O_2$; (b) it was found that the Au electrocatalyst can discriminate between the $O_2$ and $NO_x$ reductions, and that the electrocatalyst can be, through materials engineering, further improved for the optimum operation of DPV; and (c) it was demonstrated that an $NO_x$ sensor 22 for use with DPV and having a $ZrO_2$-based electrolyte can be made using inexpensive fabrication processes.

5. Conclusions

DPV is a very useful technique for measuring a very low concentration of $NO_x$. DPV reduces or completely eliminates the background current so as to enhance the resolution. With a proper electrocatalyst, DPV completely eliminates the effect of coexisting gases (e.g., $O_2$). DPV with the Au electrocatalyst discriminates between the $NO_x$ and $O_2$ reductions, and the $NO_x$ measurement is not substantially affected by varying the $O_2$ pressure from about 0.5% to about 5%. A few hundred ppm $NO_x$ were easily detected by the DPV measurement in this experiment, which can, if optimized, accurately measure a few ppm $NO_x$. If the measured value is linearly extrapolated, it is possible to obtain a few tenths of a microampere ($\mu A$) in a few ppm $NO_x$ concentration, which is easily measured by electronic instrumentation.

The sensitivity can be further improved by (1) decreasing the resistance of electrocatalyst/electrolyte interface and (2) increasing the sampling speed of the data acquisition system 23.

The major sensing components are YSZ, forming a stable material in exhaust gas. Its operational time is to about 5 to 10 years. An $NO_x$ sensor 22 based on YSZ and for use with DPV can be miniaturized and manufactured at low cost.

The present invention demonstrates the feasibility of an $NO_x$ sensor 22 based on DPV and an $O_2$ pumping cell, and demonstrates that the combination of the three components—DPV, an Au electrocatalyst, and a YSZ electrolyte—can be used to develop an $NO_x$ sensor 22 with optimized sensitivity and selectivity to $NO_x$.

It will be apparent to one of skill in the art that many variations and modifications may be made to the preferred embodiments as described above without substantially departing from the principles of the present invention. All such variations and modifications are intended to be included herein and within the scope of the present invention, as set forth in the following claims.

Wherefore, the following is claimed:

1. A sensor for accurately measuring a nitrogen oxide concentration in a gas mixture, comprising:

an electrochemical sensing cell for consuming nitrogen oxide within said gas mixture and for producing an electrical signal indicative of an amount of nitrogen oxide within said gas mixture, said sensing cell comprising an anode electrocatalyst, a cathode electrocatalyst, and a solid metal oxide electrolyte disposed therebetween; and differential pulse voltammetry means connected to said sensing cell having:

(1) pulse superimposition means for combining a pulse with a sensing cell bias imposed upon said sensing cell;

(2) measurement means for measuring said electrical signal before and during superimposition of said pulse to derive first and second sample signals; and (3) concentration derivation means for mathematically combining said first and second sample signals to derive a differential pulse voltammetry signal which is indicative of said nitrogen oxide concentration within said gas mixture;

wherein said sensing cell bias is imposed between said anode and cathode electrocatalysts and across said electrolyte, said cathode electrocatalyst for decomposing said nitrogen oxide said electrolyte capable of conducting oxide ions at high temperatures above 2000° C.

2. The sensor system of claim 1, further comprising an electrochemical pumping cell for consuming oxygen within said gas mixture.

3. The sensor system of claim 2, wherein said pumping cell and said sensing cell are partially exposed to a cavity having only a single hole for ingress of said gas mixture into said cavity.

4. The sensor system of claim 1, wherein said an electrolyte comprising zirconia.

5. The sensor system of claim 1, wherein said cathode sensing cell comprises electrocatalyst comprises a metal oxide perovskite, said cathode electrocatalyst being arranged in said sensing cell to consume said nitrogen oxide.

6. The sensor system of claim 1, wherein said cathode electrocatalyst comprises gold for decomposing said nitrogen oxide.

7. The sensor system of claim 1, wherein said cathode electrocatalyst comprises platinum for decomposing said nitrogen oxide.

8. The sensor system of claim 1, wherein said bias exhibits a step function waveform.

9. The sensor system of claim 1, further comprising a porous layer shielding said cathode electrocatalyst of said sensing cell, said porous layer being permeable to said gas mixture for permitting passage of said gas mixture therethrough to said cathode electrocatalyst.

10. The sensor system of claim 1, wherein said cathode electrocatalyst comprises gold and said electrolyte comprises yttria-stabilized-zirconia.

11. A sensor system for measuring nitrogen oxide in a high temperature exhaust gas emitted from a gas combustion process, comprising:

an electrochemical sensing cell including a cathode electrocatalyst and an anode electrocatalyst sandwiching a solid metal oxide electrolyte layer that is permeable to oxide ions at high temperatures above 200° C., wherein said sensing cell is for consuming said nitrogen oxide within said exhaust gas and for producing an electrical signal indicative of an amount of said nitrogen oxide within said exhaust gas; and differential pulse voltammetry means connected to said sensing cell for enhancing sensitivity and selectivity of said electrolyte and for generating a differential pulse voltammetry signal indicative of said nitrogen oxide concentration in said exhaust gas.

12. The sensor system of claims 11, wherein sad DPV means includes:

(1) pulse superimposition means for combining a pulse with a sensing cell bias imposed between said cathode and anode electrocatalyst and across said electrolyte;

(2) measurement means for measuring said electrical signal before and during superimposition of said pulse to derive first and second sample signals; and (3) concentration derivation means for mathematically combining said first and second sample signals to derive said differential pulse voltammetry signal which is indicative of said nitrogen oxide concentration within said gas mixture.

13. The sensor system of claim 11, further comprising a porous layer shielding said cathode electrocatalyst.

14. The sensor system of claim 11, further comprising an electrochemical pumping cell for consuming oxygen within said exhaust gas.

15. The sensor system of claim 14, wherein reduction reactions at said sensing cell and said pumping cell occur at different electrical potentials.

16. The sensor system of claim 14, wherein said pumping cell and said sensing cell are partially exposed to a cavity having only one hole for ingress of said exhaust gas into said cavity.

* * * * *